(12) United States Patent
Zamore et al.

(10) Patent No.: US 7,893,036 B2
(45) Date of Patent: *Feb. 22, 2011

(54) IN VIVO PRODUCTION OF SMALL INTERFERING RNAS THAT MEDIATE GENE SILENCING

(75) Inventors: Phillip D. Zamore, Northboro, MA (US); Juanita McLachlan, Worcester, MA (US); Gyoergy Hutvagner, Worcester, MA (US); Alla Grishok, Shrewsbury, MA (US); Craig C. Mello, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 148 days.

This patent is subject to a terminal disclaimer.

(21) Appl. No.: 12/079,531

(22) Filed: Mar. 26, 2008

(65) Prior Publication Data

US 2008/0200420 A1    Aug. 21, 2008

Related U.S. Application Data

(63) Continuation of application No. 10/195,034, filed on Jul. 12, 2002, now Pat. No. 7,691,995.

(60) Provisional application No. 60/305,185, filed on Jul. 12, 2001.

(51) Int. Cl.
    *A01N 43/04* (2006.01)
    *A61K 31/70* (2006.01)
(52) U.S. Cl. ..................................... 514/44
(58) Field of Classification Search ............. 514/44
    See application file for complete search history.

(56) References Cited

U.S. PATENT DOCUMENTS

| | | | |
|---|---|---|---|
| 5,208,149 A | 5/1993 | Inouye | |
| 5,576,208 A | 11/1996 | Monia et al. | |
| 5,624,803 A | 4/1997 | Noonberg et al. | |
| 5,631,146 A | 5/1997 | Szostak et al. | |
| 5,674,683 A | 10/1997 | Kool | |
| 5,770,580 A | 6/1998 | Ledley et al. | |
| 5,898,031 A | 4/1999 | Crooke | |
| 5,972,704 A | 10/1999 | Draper et al. | |
| 5,998,203 A | 12/1999 | Matulic-Adamic et al. | |
| 6,022,863 A | 2/2000 | Peyman | |
| 6,057,153 A | 5/2000 | George et al. | |
| 6,183,959 B1 * | 2/2001 | Thompson | 435/6 |
| 6,476,205 B1 | 11/2002 | Buhr et al. | |
| 6,506,099 B1 | 1/2003 | Bartlett | |
| 6,506,559 B1 | 1/2003 | Driver et al. | |
| 6,531,647 B1 | 3/2003 | Baulcombe et al. | |
| 6,573,099 B2 | 6/2003 | Graham | |
| 6,635,805 B1 | 10/2003 | Baulcombe et al. | |
| 6,939,712 B1 | 9/2005 | Bahramian et al. | |
| 7,056,704 B2 | 6/2006 | Tuschl et al. | |
| 7,078,196 B2 | 7/2006 | Tuschl et al. | |
| 7,691,995 B2 * | 4/2010 | Zamore et al. | 536/24.5 |
| 2001/0008771 A1 | 7/2001 | Seibel et al. | |
| 2002/0086356 A1 | 7/2002 | Tuschl et al. | |
| 2002/0132257 A1 | 9/2002 | Giordano et al. | |
| 2002/0137210 A1 | 9/2002 | Churikov | |
| 2002/0160393 A1 | 10/2002 | Symonds et al. | |
| 2002/0162126 A1 | 10/2002 | Beach et al. | |
| 2003/0051263 A1 | 3/2003 | Fire et al. | |
| 2003/0055020 A1 | 3/2003 | Fire et al. | |
| 2003/0056235 A1 | 3/2003 | Fire et al. | |
| 2003/0064945 A1 | 4/2003 | Akhtar et al. | |
| 2003/0084471 A1 | 5/2003 | Beach et al. | |
| 2003/0108923 A1 | 6/2003 | Tuschl et al. | |
| 2003/0180756 A1 | 9/2003 | Shi et al. | |
| 2003/0190654 A1 | 10/2003 | Heidenreich et al. | |
| 2003/0198627 A1 | 10/2003 | Arts et al. | |
| 2004/0002077 A1 | 1/2004 | Taira et al. | |
| 2004/0018999 A1 | 1/2004 | Beach et al. | |
| 2004/0038921 A1 | 2/2004 | Kreutzer et al. | |
| 2004/0053411 A1 * | 3/2004 | Cullen et al. | 435/455 |

(Continued)

FOREIGN PATENT DOCUMENTS

CA      2359180 A1    8/2000

(Continued)

OTHER PUBLICATIONS

Alexeev, Vitali (2000) "Localized in vivo genotypic and phenotypic correction of the albino mutation in skin by RNA-DNA oligonucleotide" Nature 18: 43-47.

(Continued)

*Primary Examiner*—Brian Whiteman
(74) *Attorney, Agent, or Firm*—Nelson Mullins Riley & Scarborough LLP; Debra J. Milasincic, Esq.; James H. Velema, Esq.

(57) ABSTRACT

The invention provides engineered RNA precursors that when expressed in a cell are processed by the cell to produce targeted small interfering RNAs (siRNAs) that selectively silence targeted genes (by cleaving specific mRNAs) using the cell's own RNA interference (RNAi) pathway. By introducing nucleic acid molecules that encode these engineered RNA precursors into cells in vivo with appropriate regulatory sequences, expression of the engineered RNA precursors can be selectively controlled both temporally and spatially, i.e., at particular times and/or in particular tissues, organs, or cells.

164 Claims, 6 Drawing Sheets

U.S. PATENT DOCUMENTS

| | | |
|---|---|---|
| 2004/0086884 A1 | 5/2004 | Beach et al. |
| 2004/0229266 A1 | 11/2004 | Tuschl et al. |
| 2004/0259248 A1 | 12/2004 | Tuschl et al. |
| 2005/0026278 A1 | 2/2005 | Tuschl et al. |
| 2005/0048647 A1 | 3/2005 | Taira et al. |
| 2005/0197315 A1 | 9/2005 | Taira et al. |
| 2005/0214851 A1 | 9/2005 | Arts et al. |
| 2005/0282764 A1 | 12/2005 | Bahramian et al. |

FOREIGN PATENT DOCUMENTS

| | | |
|---|---|---|
| DE | 19903713.2 | 5/2000 |
| DE | 19956568 A1 | 8/2000 |
| DE | 10100586 C1 | 4/2002 |
| DE | 20023125 U1 | 6/2003 |
| EP | 0649467 B1 | 9/1998 |
| EP | 01123453 .1 * | 9/2001 |
| EP | 1214945 A2 | 6/2002 |
| EP | 1214945 A3 | 6/2002 |
| EP | 1144623 B1 | 8/2002 |
| EP | 0983370 B1 | 9/2003 |
| EP | 1444346 B1 | 8/2004 |
| EP | 1352061 B1 | 5/2006 |
| EP | 1873259 A1 | 1/2008 |
| GB | 2353282 B1 | 4/2003 |
| WO | WO-94/01550 | 1/1994 |
| WO | 96/29097 A1 | 9/1996 |
| WO | WO-98/53083 B1 | 11/1998 |
| WO | WO-99/14226 B1 | 3/1999 |
| WO | WO-99/32619 | 7/1999 |
| WO | WO-99/49029 | 9/1999 |
| WO | WO-99/53050 | 10/1999 |
| WO | 99/64582 A2 | 12/1999 |
| WO | WO-99/61631 | 12/1999 |
| WO | WO-00/01846 | 1/2000 |
| WO | 00/11154 A1 | 3/2000 |
| WO | WO-00/31271 B1 | 6/2000 |
| WO | 00/49035 A1 | 8/2000 |
| WO | WO-00/44895 | 8/2000 |
| WO | 00/52188 A1 | 9/2000 |
| WO | 00/53745 A1 | 9/2000 |
| WO | WO-00/63364 | 10/2000 |
| WO | 01/36646 A1 | 5/2001 |
| WO | 01/49844 A1 | 7/2001 |
| WO | 01/70949 A1 | 9/2001 |
| WO | WO-01/75164 A2 | 10/2001 |
| WO | WO-01/92513 A1 | 12/2001 |
| WO | WO-02/44321 A2 | 6/2002 |
| WO | WO-02/055692 A2 | 7/2002 |
| WO | WO-02/059300 A2 | 8/2002 |
| WO | WO-02/061034 B1 | 8/2002 |
| WO | WO-02/066638 A1 | 8/2002 |
| WO | WO-02/068635 A2 | 9/2002 |
| WO | 03/006477 A1 | 1/2003 |
| WO | 03/012082 A2 | 2/2003 |
| WO | 03/020931 A2 | 3/2003 |
| WO | WO-03/033700 A1 | 4/2003 |
| WO | WO-03/046173 A1 | 6/2003 |
| WO | WO-03/046186 A1 | 6/2003 |
| WO | WO-03/062394 A2 | 7/2003 |
| WO | WO-03/064621 | 7/2003 |
| WO | WO 03/093441 A2 * | 11/2003 |
| WO | WO-04/022748 | 3/2004 |
| WO | 2006/040357 A2 | 4/2006 |

OTHER PUBLICATIONS

Ambion, "RNA Interference and Gene Silencing—History and Overview." (May 20, 2002), pp. 1-10.
Ambros, Victor (2001) "microRNAs: Tiny regulators with Great potential" Cell 107: 823-826.
Bartel, David P. (2004) "MicroRNAs: Genomics, Biogenesis, Mechanism, and Function" Cell 116: 281-297.
Bartel, David P. (2004) "Micromanagers of gene expression: the potentially widespread influence of metazoan microRNAs" 5:369-400.
Baulcombe, David C. (1999) "Gene silencing: RNA makes Rna makes no protein" Current Biology. 9: R599-R601.
Bellon, Laurent (1993) "4' Thio-oligo-β-D-ribonucleotides: synthesis of β-4'-thiooligouridylates, nuclease resistance, base pairing properties, and interaction with HIV-1 reverse transcriptase" Nucleic Acids Research, 21(7): 1587-1593.
Berns, Katrien et al, "A Large-scale RNAi Screen in Human Cells Identifies New Components of the p53 Pathway," *Nature*, vol. 428, 431-437 (2004).
Boden, Daniel et al, "Enhanced Gene Silencing of Hiv-1 Specific siRNA Using MicroRNA Designed Hairpins," *Nucleic Acids Research*, vol. 32(3):1154-1158 (2004).
Brummelkamp, T.R., et al., "A System for Stable Expression of Short Interfering RNAs in Mammalian Cells", Scienceexpress, 296:550-3 (2002).
Brummelkamp, Thijn R. et al, "Loss of the Cylindromatosis Tumour Suppressor Inhibits Apoptosis by Activating Ne-$_K$B," *Nature*, vol. 424, 797-801 (2003).
Brummelkamp, Thijn (2003) "New tools for functional mammalian cancer genetics" Nature Reviews 3:781-789.
Brummelkamp, Thijn R. et al, "Stable Suppression of Tumorigenicity by Virus-mediated RNA Interference," *Cancer Cell*, vol. 2, 243-247 (2002).
Cameron, F.H. (1991). "Inhibition of gene expression by a short sense fragment." Nucleic Acids Research. 19(3): 469-475.
Carrington, James C. (2003) "Role of MicroRNAs in Plant and Animal Development" 301:336-338.
Carthew, Richard W. (2001) "Gene silencing by double-stranded RNA" Current Opinion in Cell Biology, 13: 244-248.
Castanotto, D., et al., "Functional siRNA expression from transfected PCR products", RNA, 8:11, 1454-60 (2002).
Caudy, A.A., et al., "Fragile X-related protein and VIG associate with the RNA interference machinery." Genes & Development, 16: 2491-6, (2002).
Chang, Kenneth et al, "Lessons from Nature: microRNA-based shRNA Libraries," *Nature Methods*, vol. 3(9):707-714 (2006).
Check, Ericka (2003) "RNA to the rescue?" Nature 425: 10-12.
Chen, Chang-Zheng et al, "Micro RNAs Modulate Hematopoietic Lineage Differentiation," *Science*, vol. 303, 83-86 (2004).
Cheng, Jerry C. (2003) "RNA interference and human disease" Molecular Genetics and Metabolism 80:121-128.
Chiu, Y.L., et al., "RNAi in Human Cells: Basic Structural and Functional Features of Small Interfering RNA", Molecular Cell., 10:549-61 (2002).
Chuang, Chiou-Fen et al, "Specific and heritable genetic interference by double-stranded RNA in *Arabidopsis thaliana*," PNAS, vol. 97(9):4985-4990 (2000).
Cleary, Michele A. et al, "Production of Complex Nucleic Acid Libraries Using Highly Parallel In Situ Oligonucleotide Synthesis," *Nature Methods*, vol. 1(3):241-248 (2004).
Couzin Jennifer (2004) "RNAi shows cracks in its armor" Science, 306: 1124-1125.
Crooke, Stanley T. (1995) "Kinetic characteristics of Escherichia coli RNAse H1: cleavage of various antisense oligonucleotide-RNA duplexes." Biochem J. 312: 599-608.
Cummins, Lendell L. (1995) "Characterization of fully 2'-modified oligoribonucleotide hetero-and homoduplex hybridization and nuclease sensitivity" Nucleic Acids Research. 23(11): 2019-2024.
De Mesmaeker, Alain (1995) "Backbone modifications in oligonucleotides and peptide nucleic acid systems." Current Opinion in Structural Biology. 5: 343-355.
Devroe, Eric (2004) "Therapeutic potential of retroviral RNAi vectors" Expert Opin. Biol. Ther. 4(3): 319-327.
Dickens, Ross A. et al, "Probing Tumor Phenotypes Using Stable and Regulated Synthetic microRNA Precursors," *Nature Genetics*, vol. 27(11):1289-1295 (2005).

Etemad-Moghadam, Bijan. (1995). "Asymmetrical distributed PAR-3 protein contributes to cell polarity and spindle alignment in early C. elegans embryos." Cell. 83: 743-752.

Elbashir, Sayda M., et al., "Duplexes in 21-nucleotide RNAs mediate RNA interference in cultured mammalian cells," Nature, vol. 411:494-498 (2001).

Elbashir, S.M., "Functional anatomy of siRNAs for mediating efficient RNAi in Drosophila melanogaster embryo lysate", The EMBO Journal, 20(23):6877-6888 (2001).

Evroe, E., et al., "Retrovirus-delivered siRNA"., BMC Biotechnology, vol. 2, p. 15 (2002).

Elbashir, S.M., et al, "RNA interference is mediated by 21- and 22-nucleotide RNAs", Genes & Development, 15:188-200 (2001).

Fewell, Gwen D. et al, "Vector-based RNAi Approaches for Stable, Inducible and Genome-wide screens," Drug Discovery Today, vol. 11 (21/22):975-982 (2006).

Filipowicz, Witold. (2005) "RNAi: The nuts and bolts of the RISC machine" Cell. 122: 17-20.

Flintoft, Louisa. (2003). "Virus alert." Nature Reviews Drug Discovery. 2: 512.

Freitag, Michael. (2005) "Controlling DNA methylation: many roads to one modification." Current Opinion in Genetics & Development. 15: 191-199.

Gitlin, Leonid. (2003) Nucleic acid-based immune system: the antiviral potential of mammalian RNA silencing. Journal of Virology. 77(13): 7159-7165.

Greenwood, Emma (2003) "Ever-decreasing effects" Nature Reviews Cancer. 3: 236.

Grishok, A., et al., "Target dependent accumulation of small RNAs during RNAi in C. elegans", 2001 International Worm Meeting Abstract #307.

Hammond, S.M., et al., "Post-Transcriptional Gene Silencing by Double-Stranded RNA", Nature Reviews Genetics, 2:110-119 (2001).

He, Lin et al, "MicroRNAs: Small RNAs With a Big Role in Gene Regulation," Nature, vol. 5, 522-531 (2004).

Heinrichs, Arianne. (2003). "Chop, chop" Nature Reviews Molecular Cell Biology. 4: 829.

Heinrichs, Arianne. (2003) "Down a hairpin." Nature Reviews Molecular Cell Biology. 4: 173.

Heinrichs, Arianne. (2003) "Spreading silence." Nature Reviews Molecular Cell Biology. 4: 823.

Hunter, Craig P. (1999). "Genetics: A tough of elegance with RNAi." Current Biology. 9: R440- 442.

Hunter, Christine. (2003) "missing LINKS: miRNAs and plant development." Current Opinion in Genetics & Development. 13: 372-378.

Hutvagner, György, et al., "A Cellular Function for the RNA-Interference Enzyme Dicer in the Maturation of the let-7 Small Temporal RNA," Science, vol. 293:834-838 (2001).

Hutvanger, G., et al., "Intersection of the RNA interference and small temporal RNA pathways," Meeting Abstract for Cold Spring Harbor Symposium on Eukaryotic mRNA processing, Aug. 22, 2001.

Hutvanger, G., et al., "In vitro processing of pre-let-7 RNA." 2001 RNA Society Meeting Abstracts, May 31, 2001.

Hutvagner, Gyorgy. (2002). "RNAi: nature abhors a double strand." Current Opinion in Genetics & Development. 12: 225-232.

Kawasaki, Hiroaki et al, "Short Hairpin Type of dsRNAs that are Controlled by tRNA$^{VAL}$ Promoter Significantly Induce RNAi-mediated Gene Silencing in the Cytoplasm of Human Cells," Nucleic Acids Research, vol. 31(2):700-707 (2003).

Kennerdell, Jason R. et al, "Heritable gene silencing in Drosophila using double-stranded RNA," Nature Biotechnology, vol. 17:896-898 (2000).

Ketting, Rene. (2001). "Dicer functions in RNA interference and in synthesis of small RNA involved in developmental timing in C. elegans." Genes & Development. 15: 2654-2659.

Kidner, Catherine. (2003). "Macro effects of mircoRNAs in plants." TRENDS in Genetics. 19(1)): 13-16.

Lau, Nelson C. (2001) "An abundant class of tiny RNAs with probable regulatory roles in Caenorhabditis elegans." Science. 294: 858-862.

Lee, Nan Sook et al, "Expression of Small Interfering RNAs targeted against HIV-1 rev Transcripts in Human Cells," Nature Biotechnology, vol. 19, 500-505 (2002).

Levin, J.Z., et al. "Methods of double-stranded RNA-mediated gene inactivation in Arabidopsis and their use to define an essential gene in methionine biosynthesis." , Plant Molecular Biology, 44:759-775 (2000).

Lima, Walt F. (1997). "Cleavage of single strand Rna adjacent to RNA-DNA duplex regions by Escherichia coli RNase H1" The Journal of Biological Chemistry. 272(14): 27513-27516.

Lima, Walt F. (1997). "The Influence of antisense oligonucleotide-induced RNA structure on Escherichi coli RNAse H1 activity." 272(29): 18191-18199.

Lin, Rueyling. (1999). "Policing rogue genes" Nature. 402: 128-9.

Lipardi, Concetta. (2001). "RNAi as random degradative PCR: siRNA primers covert mRNA into dsRNAs that are degraded to generate new siRNAs." Cell. 107: 297-307.

Maine, Eleanor. (2000). "A conserved mechanism for post-transcriptional gene silencing." Genome Biology. 1(3): 1018.1-1018.4.

Mallory, Allison C. (2004). "MicroRNAs: something important between the genes." Current Opinion in Plant Biology. 7: 120-125.

Mathews, Michael B. (1991). "Adenovirus Virus-Associated RNA and Translation Control." Journal of Virology. 6(11): 5657-5662.

Matzke, Marjori. (2003). "RNAi extends its reach." Science. 301: 1060-1061.

Matzke Marjori. (2001). "RNA-based silencing strategies in plants" Current Opinion in Genetics & Development. 11: 221-227.

Matzke, Marjori. (2005). RNAi-mediated pathways in the nucleus. Nature Reviews Genetics. 6: 24.

McCaffrey, et al., "RNA interference in adult mice", Nature, 418:38-9 (2002).

McManus, Michael T. et al, "Gene Silencing Using Micro-RNA Designed Hairpins," RNA, vol. 8, 842-850 (2002).

McManus, M.T., et al., "Gene Silencing in Mammals by small interfering RNAs", Nature Reviews, Oct. 2002, vol. 3, pp. 737-747.

Mello, Craig C. (2004). "Revealing the world of RNA interference." Nature. 431: 338-342.

Miyagishi, Makoto et al, "U6 Promoter-Driven siRNAs with four uridine 3' Overhangs Efficiently Suppress Targeted Gene Expression in Mammalian Cells," Nature Biotechnology, vol. 19, 497-500 (2002).

Monia, Brett P. (1993). "Evaluation of 2'-modified oligonucleotides containing 2'-deoxy gaps as antisense inhibitors of gene expression." The Journal of Biological Chemistry. 268(19): 14514-14522.

Monia, Brett P. (1992). "Selective inhibition of mutant H-ras mRNA expression by antisense oligonucleotides." The Journal of Biological Chemistry. 267(28): 19954-19962.

Monia, Brett P. (1996). "Sequence-specific antitumor activity of a phosphorthionate oligodeoxyribonucleotide targeted to human C-raf kinase supports an antisense mechanism of action in vivo." Proc. Natl. Acad. Sci USA. 93: 1 5481-15484.

Montgomery, Mary K. (1998). "RNA as a target of double-stranded RNA-mediated genetic interference in Caenorhabditis elegans." Proc. Natl. Acad. Sci. 95: 15502-15507.

Moss, Eric G. (2002). "MicroRNAs: something new under the sun." Current Biology. 12: R688-R690.

Moss, E.G., "MicroRNAs: Hidden in the Genome", Current Biology ., 12(:R138-R140 (2002).

Moss, Eric G., "Non-coding RNAs: Lightning strikes twice," Current Biology, vol. 10:R436- R439 (2000).

Novina, Carl D. (2004). "The RNAi Revolution." Nature. 430: 161-164.

Nykanen, Antti. (2001). "ATP requirements and small interfering RNA structure in the RNA interference pathway." Cell. 107: 309-321.

Paddison, Patrick J. et al, "A Resource for Large-scale RNA-interference-based Screens in Mammals," Nature, vol. 428, 427-431 (2004).

Paddison, Patrick J. et al, "Cloning of Short Hairpin RNAs for Gene Knockdown in Mammalian Cells," Nature Methods, vol. 1 (2):163-167 (2004).

Paddison, Patrick J. et al, "Short Hairpin Activated Gene Silencing in Mammalian Cells," *Methods in Molecular Biology*, Ed. Jonatha M. Gott, *Humana Press*, Totowa, New Jersey, 85-100 (2004).
Paddison, P.J., et al.,"Short hairpin RNAs (shRNAs) induce sequence-specific silencing in mammalian cells", Genes Dev., 16:948-958 (2002).
Paddison, et al., "Stable suppression of gene expression by RNAi in mammalian cells.", PNAS 99:1443-1448 (2002).
Panomics, "TranSilent siRNA Vector Mix"., Cat.# SRxxxx__., 3-19 (2003).
Parrish, Susan. (2000). "Functional anatomy of a dsRNA trigger: differential requirement for the two trigger strands in RNA interference." Molecular Cell. 6: 1077-1087.
Pasquinelli, Amy E., et al., "Conservation of the sequence and temporal expression of *let-7* heterochronic regulatory RNA," *Nature*, vol. 408:86-89 (2000).
Pasquinelli, A.E., et al. "Control of Developmental Timing by MicroRNAs and their Targets", Annu. Rev. Cell Dev. Biol., 18:495-513 (2002).
Pasquinelli, A.E. "MicroRNAs: deviants no longer", TRENDS in Genetics ., 18(4):171-173 (2002).
Paul, Cynthia P. et al, "Effective Expression of Small Interfering RNA in Human Cells," *Nature Biotechnology*, vol. 20, 505-508 (2002).
Paul, C.P., et al., "Effective expression of small interfering RNA in human cells", Nat. Biotech, 29:505-3 (2002).
Plasterk, R.H.A., "RNA Silencing: the Genome's Immune System", Science 296:1263-5 (2002).
Razin, Aharon. (1998). CpG methylation, chromatin structure, and gene silencing-a three way connection. The EMBO Journal. 17(17): 4905-4908.
Reinhart, B.J., et al., "The 21-nucleotide *let-7* RNA regulates developmental timing in *Caenorhabditis elegans*", Nature 403:901-906 (2000).
Riddihough, G., "The Other RNA World"., Science ., 296:1259 (2002).
Rossi, John. (2005). "RNAi and the P-body connection." Nature Cell Biology. 7(7): 643-644.
Schramke, Vera. (2004). "Those interfering little RNAs! Silencing and Eliminating Chromatin" Current Opinion in Genetics & Development. 14: 174-180.
Schwarz, Dianne S. (2002). "Why do miRNAs live in the miRNP?" Genes & Development. 16: 1025-1031.
Silva, Jose M. et al, "Second-generation shRNA Libraries Covering the Mouse and Human Genomes," *Nature Genetics*, vol. 37(11):1281-1288 (2005).
Siolas, Despina et al, "Synthetic shRNAs as potent RNAi Triggers," *Nature Biotechnology*, vol. 23(2):227-231 (2005).
Siomi, Haruhiko. (2004). RNA interference: a new mechanism by which FMRP acts in the normal brain? What can Drosophila teach us? Mental Retardation and Developmental Disabilities Research Reviews. 10: 68-74.
Sioud, Mouldy. (2004). Therapeutic siRNAs. Trends in Pharmalogical Sciences. 25(1): 2004.
Skipper, Magdelana. (2003). "Elegant tour de force." Nature Reviews Genetics. 4 : 79-80.
Skipper, Magdelana. (2003). Have our dreams been shattered ? Nature Reviews Genetics. 4: 671.
Slack, F.J., et al., "The *lin-41* RBCC Gene Acts in the *C. Elegans* Heterochronic Pathway between the *let-7* Regulatory RNA and the LIN-29 Transcription Factor", Mol. Cell. 5(4):659-69 (2000).
Smith, Neil A., et al., "Gene expression: Total silencing by intron-spliced hairpin RNAs," *Nature*, vol. 407:319-320 (2000).
Smyth, David R. (1997). "Cosuppression at a distance." Current Biology. 7: R793-R795.
Sontheimer, Erik J. (2005). "Assembly and function of RNA silencing complexes." Nature Reviews Molecular Cell Biology. 6: 127.
Stegmeier, Frank et al, "A Lentiviral microRNA-based System for Single-Copy Polymerase II-regulated RNA Interference in Mammalian Cells," *PNAS*, vol. 102(37):13212-13217 (2005).
Storz, G., "An Expanding Universe of Noncoding RNAs", Science 296:1260-62 (2002).
Sui, G., et al., " A DNA vector-based RNAi technology to suppress gene expression in mammalian cells", PNAS., 99:8, 5515-20 (2002).
Tavernarakis, Nekarios et al, "Heritable and inducible genetic interference by double-stranded RNA encoded by transgenes," *Nature Genetics*, vol. 24:180-183 (2000).
Tijsterman, Marcel. (2002). "The Genetics of RNA silencing." Annu. Rev. Genet. 36: 489-519.
Timmons, Lisa. (1998). "Specific interference of ingested dsRNA." Nature. 395: 854.
Tuschl, Thomas. (2003). "RNA sets the standard." Nature. 421: 220-221.
Tuschl, Thomas. (2003). "RNA silencing." Products and Perspectives Advancing Cell Discovery. Upstate Biosignals. vol. 3.
Ui-Tei, K., et al., "Sensitive assay of RNA interference in *Drosophila* and Chinese hamster cultured cells using firefly luciferase gene as target.". FEBS Letters 479:79-82 (2000).
Van de Wetering, Marc, et al, "Specific Inhibition of Gene Expression Using a Stably Integrated, Inducible Small-interfering-RNA Vector," *European Molecular Biology Organization*, vol. 4(6):609-615 (2003).
Vaucheret, Herve. (1998). "Transgene-induced gene silencing in plants." The Plant Journal. 16(6): 651-659.
Wang, Ming-Bo. (2001). "Replicating satellite RNA induces sequence-specific DNA methylation and truncated transcripts in plants." RNA. 7: 16-28.
Waterhouse, Peter M. (2003). "Exploring plant genomes by RNA-induced gene silencing." Nature Reviews Genetics. 4: 29-38.
Waterhouse, P., M., et al., "Virus resistance and gene silencing in plants can be induced by simultaneous expression of sense and antisense RNA," Proc. Natl. Acad. Sci. USA, Nov. 1998, vol. 95, pp. 13959-13964.
Westbrook, Thomas F. et al, "A Genetic Screen for Candidate Tumor Supressors Identifies Rest," *Cell*, vol. 121, 837-848 (2005).
Woo, Junsuk. (1996). "G/C-modified oligodeoxynucleotides with selective complementarity: synthesis and hybridization properties." Nucleic Acids Research. 24(13): 2470-2475.
Wu, Hongjiang. (2000). "Human RNase III is a 160-kDa protein involved in preribosomal RNA processing." The Journal of Biological Chemistry. 275(47): 36957-36965.
Wu, Hongjiang. (1999). "Properties of cloned and expressed human RNAse H1." The Journal of Biological Chemistry. 274(40): 28270-28278.
Yang, Dun. (2000). "Evidence that processed small dsRNAs may mediate sequence-specific mRNA degradatation during RNAi in Drosophila embryos." Current Biology. 10: 1191-1200.
Yang, S., et al. "Specific Double-Stranded RNA Interference in Undifferentiated Mouse Embryonic Stem Cells.", Molecular and Cellular Biology:21(22): 7807-7816 (2001).
Yu, J-Y, et al., RNA interference by expression of short-interfering RNAs and hairpin RNAs in mammalian cells, PNAS vol. 99, No. 9:6047-52 (2002).
Zamore, P.D., et al., "Ancient Pathways programmed by small RNAs", Science, 296:1265-9 (2002).
Zamore, Phillip D. (2000). "RNAi: Double-stranded RNA directs the ATP-dependent cleavage of mRNA at 21 to 23 nucleotide intervals." Cell. 101: 25-33.
Zamore, Phillip D. (2001). "RNA interference: listening to the sound of silence." Nature Structural Biology. 8(9): 746-750.
Zamore, Phillip D. (2005). "Ribo-gnome: the big world of small RNAs." Science. 309: 1519-1524.
Zeng, Yan et al, "Both Natural and Designed Micro RNAs Can Inhibit the Expression of Cognate mRnas When Expressed in Human Cells," *Molecular Cell*, vol. 9, 1327-1333 (2002).
Zeng, Yan et al, "Sequence Requirements for Micro RNA Processing and Function in Human Cells," *RNA*, vol. 9, 112-123 (2003).
Zheng, Lianxing et al, "An Approach to Genomewide Screens of Expressed Small Interfering RNAs in Mammalian Cells," *PNAS*, vol. 101(1)1 35-140 (2004).
Zhang, H. et al., "Single processing center models for human Dicer and bacterial RNase III," *Cell*, vol. 118(1):57-68 (2004).
Notice of Opposition to European Patent No. EP 1 144 623 and Opposition papers filed in EPO by Atugen AG on May 28, 2003.

Notice of Opposition to European Patent No. EP 1 144 623 and Opposition papers filed in EPO by Janssen Pharmaceutica N. V. on May 28, 2003.

Papers filed in EPO in opposition to European Patent No. EP 1 144 623 by Aventis Pharma Deutschland GmbH on May 28, 2003.

Papers filed in EPO in opposition to European Patent No. EP 1 144 623 by Dr. Martin Grund on May 28, 2003.

Papers filed in EPO in opposition to European Patent No. EP 1 144 623 by siRNA Therapeutics Inc. on May 19, 2003.

European Search Report Application No./Patent No. EP02746979.0-2101 PCT/US02/22010 dated Oct. 11, 2005.

European Search Report Application No./Patent No. EP02746979.0-2101 PCT/US02/22010 dated Dec. 28, 2005.

Caplen, Natasha J. et al., "Specific inhibition of gene expression by small double-stranded RNAs in invertebrate and vertebrate systems," *PNAS*, vol. 98(17):9742-9747 (2001).

Lewandoski, Mark et al., "Zp3-cre, a transgenic mouse line for the activation or inactivation of *lox-P*-flanked target genes specifically in the female germ line," *Current Biology*, vol. 7:148151 (1997).

Ohkawa, Jun et al., "Control of the Functional Activity of an Antisense RNA by a Tetracycline-Responsive Derivative of the Human Ug snRNA Promoter," *Human Gene Therapy*, vol. 11:577-585 (2000).

Saito, Izumi et al., "Cre/loxP-kei to Adeno Virus Vector niyoru Idenshi Hatsugen on/off Seigyoho no Oyo," *Gene & Medicine*, JVol. 2(4):606-611 (1998).

Wang, Zefeng et al., "Inhibition of *Trypanosoma brucei* Gene Expression by RNA Interference Using an Integratable Vector with Opposing T7 Promoters," *The Journal of Biological Chemistry*, vol. 275(51):40174-40179 (2000).

Zhao, Xinyang et al., "A Positioned Nucleosome on the Human U6 Promoter Allows Recruitment of SNAP by the Oct-1 POU Domain," *Molecular Cell*, vol. 7:539-549 (2001).

International Search Report for Application No. PCT/JP02/12447, dated Feb. 25, 2003.

International Search Report for Application No. PCT/JP02/11293, dated Dec. 24, 2002.

Grishok and Mello., "RNAi and Development References," Advances in Genetics, vol. 46:340-360 (2002).

Ambros, Victor, "microRNAs: Tiny Regulators with Great Potential," Cell, vol. 107:823-826 (2001).

Grosshans, H. et al., "Mirco-RNAs: small is plentiful," The Journal of Cell Biology, vol. 156(1):17-21 (2002).

Lagos-Quintana, M et al., "Indentification of Novel Genes Coding for Small Expressed RNAs," Science, vol. 294:853-858 (2001).

Lagos-Quintana, M. et al., Identification of Tissue-Specific MicroRNAs from Mouse, Current Biology, vol. 12:735-739 (2002).

Lai, et al., "Micro RNAs are complementary to 3' UTR sequence motifs that mediate negative post-transcriptional regulation," Nature Genetics, vol. 30:363-364 (2002).

Lau, N. et al., "An Abundant Class of Tiny RNAs with Probable Regulatory Role in *Caenorhabditis elegans*," Science, vol. 294:858-862 (2001).

Lee, R., et al., "An Extensive Class of Small RNAs in Caenorhabditis elegans," Science, vol. 294:862-864 (2001).

Lee, Y. et al., "MicroRNA maturation: stepwise processing and subcellular localization," The EMBO Journal, vol. 21 (17):4663-4670 (2002).

Moss, E., "RNA Interference: It's a small RNA world," Current Biology, vol. 11:R772-R775 (2001).

Mourelatos, Z. et al., "miRNPs: a novel class of ribonucleoproteins containing numerous microRNAs," Genes & Development, vol. 16:720-728 (2002).

Reinhart, B. et al., "MicroRNAs in plants," Genes & Development, vol. 16:1616-1626 (2002).

European Office Action for Application No. 02746979.0, dated Jun. 10, 2010.

Arts, Gert-Jan et al., "Adenoviral Vectors Expressing siRNAs for Discovery and Validation of Gene Function," Genome Research, vol. 13:2325-2332 (2003).

Bernstein, Emily et al., "Role for the bidentate ribonuclease in the initiation step of RNA interference," Nature, vol. 409:363-366 (2001).

Fraser, Andrew G. et al., "Functional genomic analysis of *C. elegans* chromosome I by systematic RNA interference," Nature, vol. 408:325-330 (2000).

Goguel, Valerie et al., "Short Artificial Hairpins Sequester Splicing Signals and Inhibit Yeast Pre-mRNA Splicing," Molecular and Cellular Biology, Vol. 13(11):6841-6848 (1993).

Grishok, Alla et al., "Genes and Mechanisms Related to RNA Interference Regulate Expression of the Small Temporal RNAs that Control *C. elegans* Developmental Timing," Cell, vol. 106:23-34 (2001).

Hammond, Scott M. et al., "An RNA-directed nuclease mediates post-transcriptional gene silencing in Drosophila cells," Nature, vol. 404:293-296 (2000).

Kuwabara, P.E. et al., "RNAi-Prospects for a General Technique for Determining Gene Function," Parasitology Today, vol. 16(8):347-349 (2000).

Lambeth, Luke S. et al., "Characterisation and application of a bovine U6 promoter for expression of short hairpin RNAs," BMC Biotechnology, vol. 5(13) doi:10.1186/1472-6750-5-13 (2005).

Medina, Maria Fe C. et al., "RNA polymerase III-driven expression cassettes in human gene therapy," Current Opinion in Molecular Therapeutics, vol. 1(5):580-594 (1999).

Mette, M.F. et al., "Transcriptional silencing and promoter methylation triggered by double-stranded RNA," The EMBO Journal, vol. 19(19):5194-5201 (2000).

Potter, Philip M. et al., "Construction of Adenovirus for High Level Expression of Small RNAs in Mammalian Cells, Application to a Bcl-2 Ribozyme," Molecular Biotechnology, vol. 15:105-114 (2000).

Raykov, Z. et al., "Transient suppression of transgene expresion by means of antisense oligonucleotides: a method for the production of toxin-transducing recombinant viruses," Gene Therapy, vol. 9:358-362 (2002).

Shi, Huafang et al., "Genetic interference in *Trypanosoma brucei* by heritable and inducible double-stranded RNA," RNA, vol. 6:1069-1076 (2000).

Smith, Neil A. et al., "Gene expression: Total silencing by intron-spliced hairpin RNAs," Nature, vol. 407:319-320 (2000).

Sui, Guangchao et al., "A DNA vector-based RNAi technology to suppress gene expression in mammalian cells," PNAS, vol. 99(8):5515-5520 (2002).

Svoboda, Petr et al., "Selective reduction of dormant maternal mRNAs in mouse oocytes by RNA interference," Development, vol. 127:4147-4156 (2000).

Tuschl, Thomas et al., "Targeted mRNA degradation by double-stranded RNA in vitro," Genes & Development, vol. 13:3191-3197 (1999).

Verma, Sandeep et al., "Modified Oligonucleotides: Synthesis and Strategy for Users," Annu. Rev. Biochem., vol. 67:99-134 (1998).

Vermeulen, Annaleen et al., "The contributions of dsRNA structure to Dicer specificity and efficiency," RNA, vol. 11:674-682 (2005).

Vickers, Timothy A. et al., "Efficient Reduction of Target RNAs by Small Interfering RNA and RNase H-dependent Antisense Agents," The Journal of Biological Chemistry, vol. 278(9):7108-7118 (2003).

Wang, Ming-Bo et al., "High-efficiency silencing of a Beta-glucuronidase gene in rice is correlated with repetitive transgene structure but is independent of DNA methylation," Plant Molecular Biology, vol. 43:67-82 (2000).

Wianny, Florence et al., "Specific interference with gene function by double-stranded RNA in early mouse development," Nature Cell Biology, vol. 2:70-75 (2000).

Wikipedia, "Small interfering RNA," obtained online at: http://en.wikipedia.org/wiki/SiRNA (2010).

Yang, Yih-Sheng et al., "Directional cloning of an oligonucleotide fragment into a single restriction site," Journal of Immunological Methods, Vol. 181:137-140 (1995).

\* cited by examiner (SEQ ID NO:1)

(SEQ ID NO:2)

(SEQ ID NO:3)

FIG. 2D

```
                                                G  A   U
5'-GGCAAAUGCUUGAAGCAGCUCUGGAGUA U A AU U
   ······························ · ··
3'-UCGUUUACGAACUUCGUCGAGACCUCAU A  UA U
                                   C    U
```

(SEQ ID NO:4)

FIG. 2E

```
                                            G
5'-GGCAAAUGCUUGAAGCAGCUCUGGAGUA G
   ······························
3'-UCGUUUACGAACUUCGUCGAGACCUCAU G
                                  G
```

(SEQ ID NO:5)

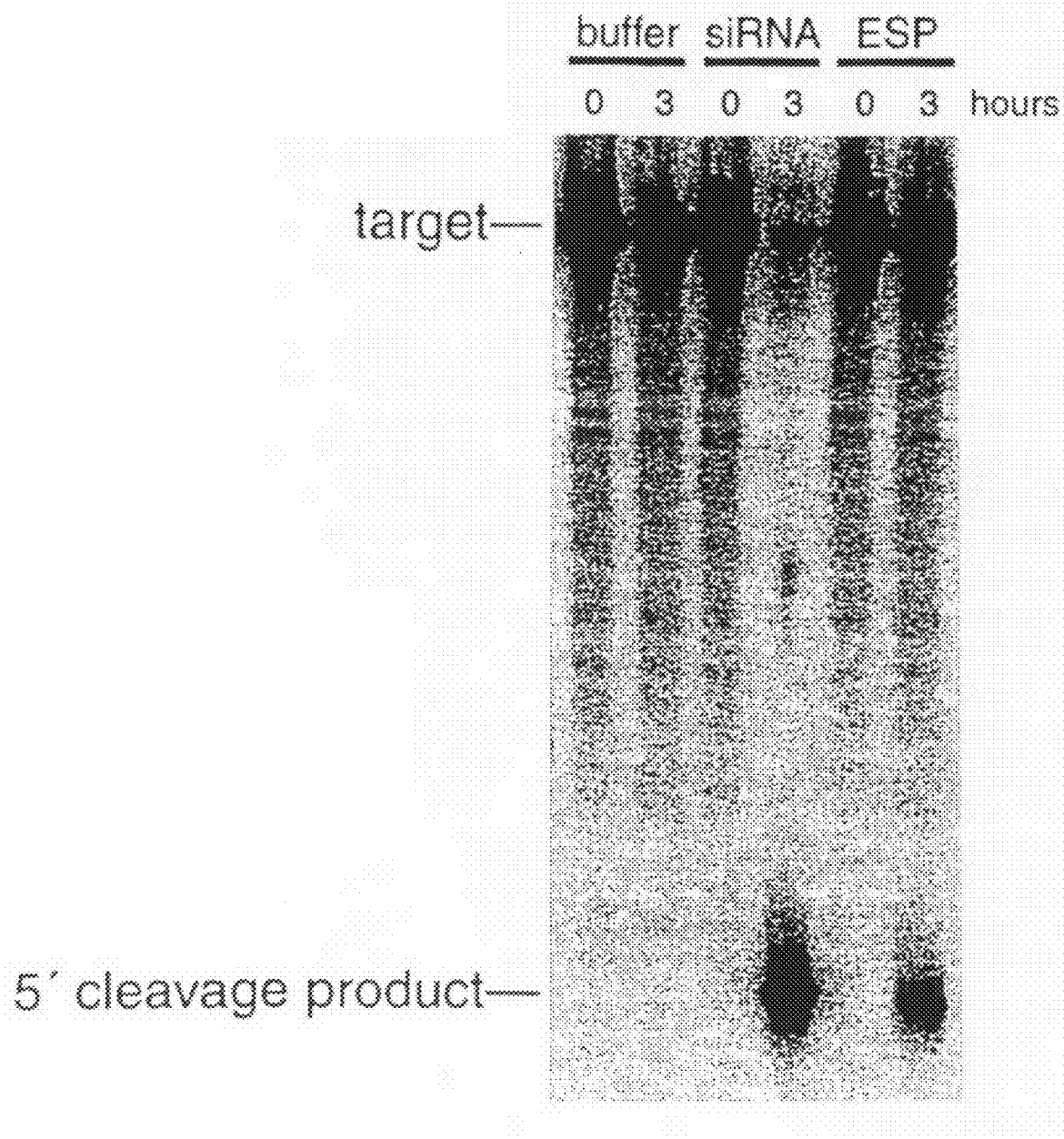

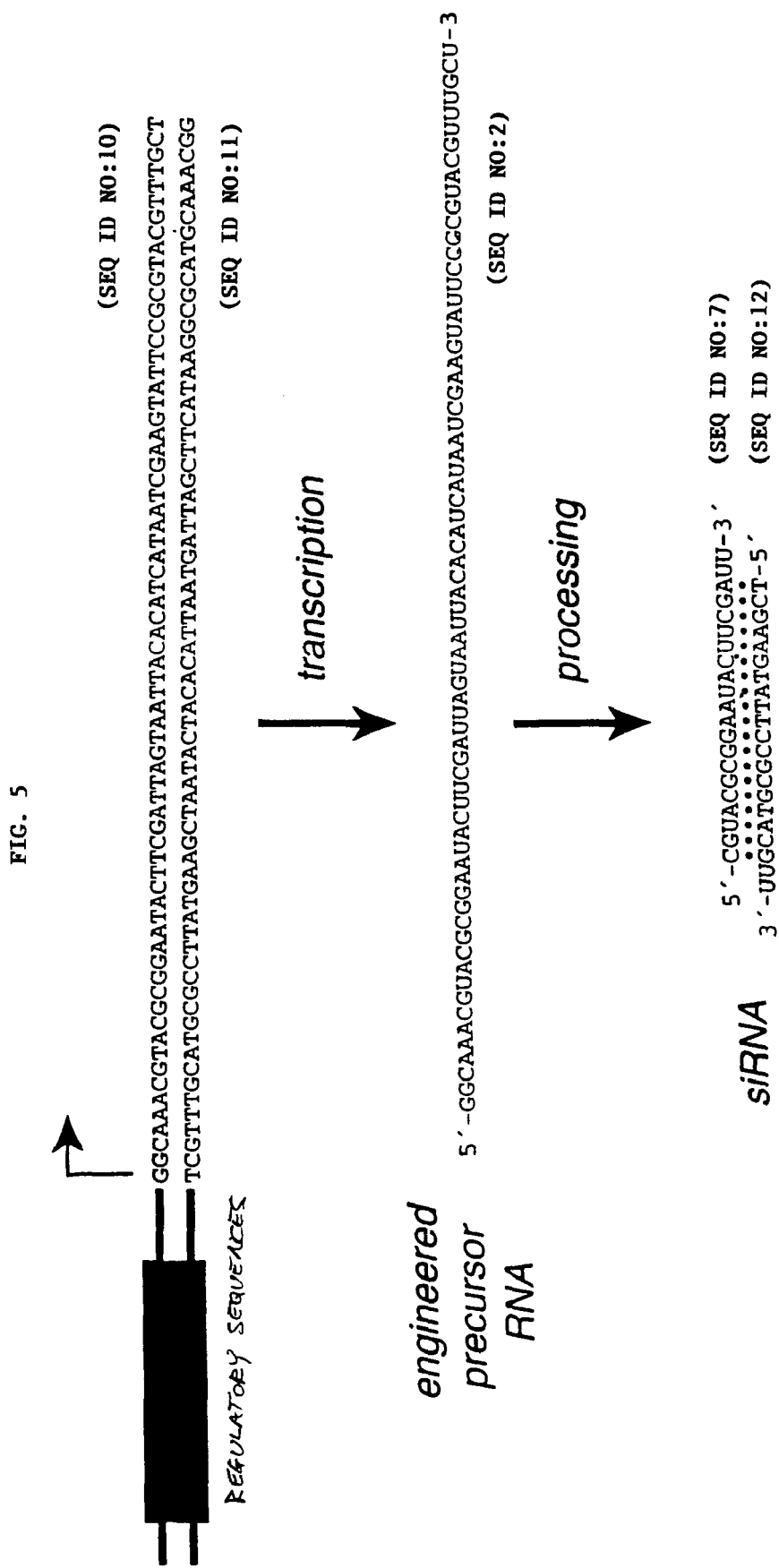

SEQUENCE LISTING

<160> NUMBER OF SEQ ID NOS: 21

<210> SEQ ID NO 1
<211> LENGTH: 72
<212> TYPE: RNA
<213> ORGANISM: Homo sapiens

<400> SEQUENCE: 1
ggcaaauuga gguaguaggu uguauaguag uaauuacaca ucauacuaua caaugugcua      60
gcuuucuuug cu      72

<210> SEQ ID NO 2
<211> LENGTH: 70
<212> TYPE: RNA
<213> ORGANISM: Artificial Sequence
<220> FEATURE:
<223> OTHER INFORMATION: Synthetically generated oligonucleotide

<400> SEQUENCE: 2
ggcaaacgua cgcggaauac uucgauuagu aauuacacau cauaaucgaa guauccgcg      60 uacguuugcu      70

```
<210> SEQ ID NO 3
<211> LENGTH: 70
<212> TYPE: RNA
<213> ORGANISM: Artificial Sequence
<220> FEATURE:
<223> OTHER INFORMATION: Synthetically generated oligonucleotide

<400> SEQUENCE: 3
ggcaaaugcu ugaagcagcu cuggaguagu aauuacacau cauacuccag agcugcuuca    60
agcauuugcu                                                          70

<210> SEQ ID NO 4
<211> LENGTH: 69
<212> TYPE: RNA
<213> ORGANISM: Artificial Sequence
<220> FEATURE:
<223> OTHER INFORMATION: Synthetically generated oligonucleotide

<400> SEQUENCE: 4
ggcaaaugcu ugaagcagcu cuggaguagu aauuuuauc auacuccaga gcugcuucaa    60
gcauuugcu                                                           69

<210> SEQ ID NO 5
<211> LENGTH: 60
<212> TYPE: RNA
<213> ORGANISM: Artificial Sequence
<220> FEATURE:
<223> OTHER INFORMATION: Synthetically generated oligonucleotide

<400> SEQUENCE: 5
ggcaaaugcu ugaagcagcu cuggaguagg gguacuccag agcugcuuca agcauuugcu    60

<210> SEQ ID NO 6
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 6
ucgaaguauu ccgcguacgu g                                             21

<210> SEQ ID NO 7
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 7
cguacgcgga auacuucgau u                                             21

<210> SEQ ID NO 8
<211> LENGTH: 72
<212> TYPE: RNA
<213> ORGANISM: Artificial Sequence
<220> FEATURE:
<223> OTHER INFORMATION: Synthetically generated oligonucleotide

<400> SEQUENCE: 8
ggcaaaucgu acgcggaaua cuucgaaaag uaauuacaca ucauuuucga aguauuccgc    60
guacgauuug cc                                                       72

<210> SEQ ID NO 9
```

```
<211> LENGTH: 72
<212> TYPE: RNA
<213> ORGANISM: Artificial Sequence
<220> FEATURE:
<223> OTHER INFORMATION: Synthetically generated oligonucleotide

<400> SEQUENCE: 9
ggcaaauucg aaguauuccg cguacgugag uaauuacaca ucaucacgua cgcggaauac      60
uucgaauuug cc                                                         72

<210> SEQ ID NO 10
<211> LENGTH: 70
<212> TYPE: DNA
<213> ORGANISM: Artificial Sequence
<220> FEATURE:
<223> OTHER INFORMATION: Synthetically generated oligonucleotide

<400> SEQUENCE: 10
ggcaaacgta cgcggaatac ttcgattagt aattacacat cataatcgaa gtattccgcg      60
tacgtttgct                                                            70

<210> SEQ ID NO 11
<211> LENGTH: 70
<212> TYPE: DNA
<213> ORGANISM: Artificial Sequence
<220> FEATURE:
<223> OTHER INFORMATION: Synthetically generated oligonucleotide

<400> SEQUENCE: 11
ggcaaacgta cgcggaatac ttcgattagt aattacacat cataatcgaa gtattccgcg      60
tacgtttgct                                                            70

<210> SEQ ID NO 12
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 12
tcgaagtatt ccgcgtacgu u                                               21

<210> SEQ ID NO 13
<211> LENGTH: 4
<212> TYPE: RNA
<213> ORGANISM: Artificial Sequence
<220> FEATURE:
<223> OTHER INFORMATION: exemplary sequence
<221> NAME/KEY: misc_feature
<222> LOCATION: 2
<223> OTHER INFORMATION: n = a, c, g, or u

<400> SEQUENCE: 13 gnra                                                                   4

<210> SEQ ID NO 14
<211> LENGTH: 4
<212> TYPE: RNA
<213> ORGANISM: Artificial Sequence
<220> FEATURE:
<223> OTHER INFORMATION: exemplary sequence

<400> SEQUENCE: 14 gggg                                                                   4
```

```
<210> SEQ ID NO 15
<211> LENGTH: 4
<212> TYPE: RNA
<213> ORGANISM: Artificial Sequence
<220> FEATURE:
<223> OTHER INFORMATION: exemplary sequence

<400> SEQUENCE: 15 uuuu                                                                          4

<210> SEQ ID NO 16
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 16
cguacgcgga auacuucgau u                                                      21

<210> SEQ ID NO 17
<211> LENGTH: 90
<212> TYPE: DNA
<213> ORGANISM: Artificial Sequence
<220> FEATURE:
<223> OTHER INFORMATION: Synthetically generated oligonucleotide

<400> SEQUENCE: 17
gcgtaatacg actcactata ggcaaacgta cgcggaatac ttcgattagt aattacacat            60
cataatcgaa gtattccgcg tacgtttgct                                             90

<210> SEQ ID NO 18
<211> LENGTH: 92
<212> TYPE: DNA
<213> ORGANISM: Artificial Sequence
<220> FEATURE:
<223> OTHER INFORMATION: Synthetically generated oligonucleotide

<400> SEQUENCE: 18
tgtagtcacg tacgcggaat acttcgaaga aacgagtaat tactaaatcg aagtattccg            60
cgtacgtttg cctatagtga gtcgtattac gc                                          92

<210> SEQ ID NO 19
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 19
gtaatacgac tcactatag                                                         19

<210> SEQ ID NO 20
<211> LENGTH: 90
<212> TYPE: DNA
<213> ORGANISM: Artificial Sequence
<220> FEATURE:
<223> OTHER INFORMATION: Synthetically generated oligonucleotide

<400> SEQUENCE: 20
ggcaaattcg aagtattccg cgtacgtgat gatgtgtaat tactcacgta cgcggaatac            60
ttcgaatttg cctatagtga gtcgtattac                                             90
```

-continued

```
<210> SEQ ID NO 21
<211> LENGTH: 90
<212> TYPE: DNA
<213> ORGANISM: Artificial Sequence
<220> FEATURE:
<223> OTHER INFORMATION: Synthetically generated oligonucleotide

<400> SEQUENCE: 21
ggcaaatcgt acgcggaata cttcgaaaat gatgtgtaat tacttttcga agtattccgc      60
gtacgatttg cctatagtga gtcgtattac                                      90
```

IN VIVO PRODUCTION OF SMALL INTERFERING RNAS THAT MEDIATE GENE SILENCING

RELATED APPLICATIONS

This application is continuation of U.S. Utility application Ser. No. 10/195,034 (now U.S. Pat. No. 7,691,995), entitled "In Vivo Production of Small Interfering RNAs that Mediate Gene Silencing" (filed Jul. 12, 2002), which claims the benefit of U.S. Provisional Patent Application Ser. No. 60/305,185, entitled "In Vivo Production of Small Interfering RNAs that Mediate Gene Silencing" (filed Jul. 12, 2001). The entire contents of the above-referenced patent applications are incorporated herein by this reference.

STATEMENT AS TO FEDERALLY SPONSORED RESEARCH

This invention was made with government support under grant no. GM62862-01 awarded by the National Institutes of Health. The government has certain rights in the invention.

TECHNICAL FIELD

This invention relates to ribonucleic acid interference (RNAi), and more particularly to RNAi in vivo.

BACKGROUND

RNAi is the sequence-specific, post-transcriptional silencing of a gene's expression by double-stranded RNA. RNAi is mediated by 21 to 25 nucleotide, double-stranded RNA molecules referred to as small interfering RNAs (siRNAs) that are derived by enzymatic cleavage of long, double-stranded RNA in cells. siRNAs can also be synthesized chemically or enzymatically outside of cells and then delivered to cells (e.g., by transfection) (see, e.g., Fire et al., 1998, "Potent and specific genetic interference by double-stranded RNA in *Caenorhabditis elegans*," Nature, 391:806-11; Tuschl et al., 1999, "Targeted mRNA degradation by double-stranded RNA in vitro," Genes Dev., 13:3191-7; Zamore et al., 2000, "RNAi: double-stranded RNA directs the ATP-dependent cleavage of mRNA at 21 to 23 nucleotide intervals," Cell, 101:25-33; Elbashir et al., 2001, "Duplexes of 21-nucleotide RNAs mediate RNA interference in mammalian cell culture," Nature, 411:494-498; and Elbashir et al., 2001, "RNA interference is mediated by 21- and 22-nucleotide RNAs," Genes Dev., 15:188-200.

Double-stranded siRNAs mediate gene silencing by targeting for disruption or cleavage messenger RNAs (mRNAs) that contain the sequence of one strand of the siRNA. siRNAs introduced into mammalian cells by transfection mediate sequence-specific gene silencing, whereas long, double-stranded RNA induces sequence non-specific responses.

SUMMARY

The invention is based on the discovery of new artificial, engineered RNA precursors, that when expressed in a cell, e.g., in vivo, are processed by the cell to produce targeted siRNAs that selectively silence target genes (by targeting specific mRNAs for cleavage) using the cell's own RNAi pathway. By introducing nucleic acid molecules that encode these engineered RNA precursors into cells in vivo with appropriate regulatory sequences (e.g., a transgene in a vector such as a plasmid), expression of the engineered RNA precursors can be selectively controlled both temporally and spatially, i.e., at particular times and/or in particular tissues, organs, or cells.

In general, the invention features an isolated nucleic acid molecule including a regulatory sequence operably linked to a nucleic acid sequence that encodes an engineered ribonucleic acid (RNA) precursor, wherein the precursor includes: (i) a first stem portion comprising a sequence of at least 18 nucleotides that is complementary to a sequence of a messenger RNA (mRNA) of a target gene; (ii) a second stem portion comprising a sequence of at least 18 nucleotides that is sufficiently complementary to the first stem portion to hybridize with the first stem portion to form a duplex stem (e.g., a stem that can be processed by the enzyme Dicer); and (iii) a loop portion that connects the two stem portions. In another aspect, the invention features the engineered RNA itself. The RNA precursor targets a portion of the mRNA of the target gene, disrupts translation of the mRNA by cleaving the mRNA, and thereby prevents expression of the protein to be inhibited. The target genes can be, for example, human genes, e.g., mutant human genes, e.g., having a point mutation, or they can be viral or other genes.

In these molecules and precursors, the first stem portion can be fully complementary (i.e., completely complementary) to the mRNA sequence. In other embodiments, the stem portion can be complementary, i.e., the sequence can be substantially complementary (e.g., there can be no more than one or two mismatches over a stretch of 20 nucleotides). Similarly, the second stem portion can fully or substantially complementary to the first stem portion. The first stem portion can be located at a 5' or 3' end of the RNA precursor.

In these precursors, the loop portion can include at least 4, 7, or 11, or more nucleotides, and the sequence of the mRNA is located from 100 to 300 nucleotides 3' of the start of translation of the mRNA. The sequence of the mRNA can be located in a 5' untranslated region (UTR) or a 3' UTR of the mRNA. The first and second stem portions can each include about 18 to about 30 nucleotides, or about 22 to about 28 nucleotides. The first and second stem portions can each have the same number of nucleotides, or one of the first and second stem portions can have 1 to 4 more nucleotides than the other stem portion. These overhanging nucleotides can all be uracils.

In these nucleic acid molecules, the regulatory sequence can be a Pol III or Pol II promoter, and can be constitutive or inducible. In specific embodiments, the engineered RNA precursor can have the sequence set forth in SEQ ID NO: 1, 2, 3, 4, 5, 8, or 9, and the nucleic acid molecule can have the sequence set forth in SEQ ID NO:10, 11, 17, 18, 20, or 21, or a complement thereof.

In other embodiments, the invention also features vectors, e.g., plasmids or viral (e.g., retroviral) vectors, that include the new nucleic acid molecules.

In another aspect, the invention includes host cells, e.g., mammalian cells, that contain the new nucleic acid molecules. The invention also includes transgenes that include the new nucleic acid molecules.

In another aspect of the invention, the invention features transgenic, non-human animals, one or more of whose cells include a transgene containing one or more of the new nucleic acid molecules, wherein the transgene is expressed in one or more cells of the transgenic animal resulting in the animal exhibiting ribonucleic acid interference (RNAi) of the target gene by the engineered RNA precursor. For example, the transgene can be expressed selectively in one or more cardiac cells, lymphocytes, liver cells, vascular endothelial cells, or spleen cells. In these animals, the regulatory sequence can be constitutive or inducible, or the regulatory sequence can be tissue specific. In some embodiments, the regulatory sequence can a Pol III or Pol II promoter, and can be a an exogenous sequence. These transgenic animals can be non-human primates or rodents, such as mice or rats, or other animals (e.g., other mammals, such as goats or cows; or birds) described herein.

The invention also includes cells derived from the new transgenic animals. For example, these cells can be a lymphocyte, a hematopoietic cell, a liver cell, a cardiac cell, a vascular endothelial cell, or a spleen cell.

In another aspect, the invention includes methods of inducing ribonucleic acid interference (RNAi) of a target gene in a cell, e.g., in an animal or in culture. The new methods include obtaining a transgenic animal comprising a transgene including a nucleic acid molecule encoding an engineered RNA precursor and an inducible promoter; and inducing the cell to express the precursor to form a small interfering ribonucleic acid (siRNA) within the cell, thereby inducing RNAi of the target gene in the animal.

Alternatively, the methods include obtaining a host cell; culturing the cell; and enabling the cell to express the RNA precursor to form a small interfering ribonucleic acid (siRNA) within the cell, thereby inducing RNAi of the target gene in the cell.

A "transgene" is any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A "transformed cell" is a cell into which (or into an ancestor of which) has been introduced, by means of recombinant DNA techniques, a nucleic acid molecule or transgene encoding an engineered RNA precursor.

As used herein, the term "operably linked" means that a selected nucleic acid sequence, e.g., encoding an engineered RNA precursor, is in proximity with a promoter, e.g., a tissue-specific promoter, to allow the promoter to regulate expression of the selected nucleic acid sequence. In addition, the promoter is located upstream of the selected nucleic acid sequence in terms of the direction of transcription and translation.

By "promoter" is meant a nucleic acid sequence that is sufficient to direct transcription. A tissue-specific promoter affects expression of the selected nucleic acid sequence in specific cells, e.g., hematopoietic cells, or cells of a specific tissue within an animal, e.g., cardiac, muscle, or vascular endothelium. The term also covers so-called "leaky" promoters, which regulate expression of a selected nucleic acid sequence primarily in one tissue, but cause expression in other tissues as well. Such promoters also may include additional DNA sequences that are necessary for expression, such as introns and enhancer sequences.

By "transgenic" is meant any cell that includes a nucleic acid, e.g., DNA sequence, that is inserted by artifice into a cell and becomes part of the genome of an organism that develops from that cell. A "transgenic animal" means an animal that includes a transgene that is inserted into an embryonal cell and becomes a part of the genome of the animal which develops from that cell, or an offspring of such an animal. In the transgenic animals described herein, the transgene causes specific tissue cells to express an engineered RNA precursor. Any animal that can be produced by transgenic technology is included in the invention, although mammals are preferred. Preferred mammals include non-human primates, sheep, goats, horses, cattle, pigs, rabbits, and rodents such as guinea pigs, hamsters, rats, gerbils, and, preferably, mice.

An "isolated nucleic acid molecule or sequence" is a nucleic acid molecule or sequence that is not immediately contiguous with both of the coding sequences with which it is immediately contiguous (one on the 5' end and one on the 3' end) in the naturally occurring genome of the organism from which it is derived. The term therefore includes, for example, a recombinant DNA or RNA that is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide sequence.

A "target gene" is a gene whose expression is to be selectively inhibited or "silenced." This silencing is achieved by cleaving the mRNA of the target gene by an siRNA that is created from an engineered RNA precursor by a cell's RNAi system. One portion or segment of a duplex stem of the RNA precursor is an anti-sense strand that is complementary, e.g., fully complementary, to a section of about 18 to about 40 or more nucleotides of the mRNA of the target gene.

The term "engineered," as in an engineered RNA precursor, or an engineered nucleic acid molecule, indicates that the precursor or molecule is not found in nature, in that all or a portion of the nucleic acid sequence of the precursor or molecule is created or selected by man. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention provides several advantages. For example, the invention improves on and overcomes a significant deficiency in the prior art. Prior methods for inducing RNAi in mammalian cells using siRNAs were restricted to cell cultures. The new methods extend RNAi to whole animals, e.g., mammals, and thus allow RNAi to be targeted to specific cell types, organs, or tissues, and/or to specific developmental stages.

In addition, this technology simplifies and lowers the cost of siRNA construction, because DNA molecules are relatively inexpensive to make. Thus, large populations of plasmids or other vectors can be prepared, each containing a nucleic acid molecule that encodes an engineered RNA precursor that targets a particular gene, can be easily prepared, e.g., in an array format. In addition, the new nucleic acid molecules can be introduced into a variety of cells, which can be cultured in vitro using known techniques. Furthermore, the new methods enable the long-term, e.g., permanent, reduction of targeted gene expression in cell lines, because siRNAs are transient, but a transgenic hairpin provides a long-lasting supply of siRNAs.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 2B to 2E are schematic representations of synthetic, engineered RNA precursors (SEQ ID NOS:2, 3, 4, and 5).

FIG. 3 is an autoradiograph showing the results of an assay for determining whether an engineered RNA precursor can promote cleavage of the target mRNA in vitro in a standard RNAi reaction.

FIGS. 4A to 4C are schematic representations of synthetic luciferase siRNA (4A; SEQ ID NOS: 6 and 7), and 5' and 3' synthetic, engineered RNA precursors (4B; SEQ ID NO:8; and 4C; SEQ ID NO:9).

FIG. 4E is an autoradiograph showing the results of an assay for determining whether the 5' and 3' synthetic, engineered RNA precursors of FIGS. 4B and 4C can promote cleavage of the target mRNA in vitro in a standard RNAi reaction.

FIG. 5 is a schematic diagram of transgene encoding an engineered RNA precursor (SEQ ID NO:2) and the transcription and processing of the precursor to form a double-stranded siRNA (SEQ ID NO:7 and SEQ ID NO:12).

DETAILED DESCRIPTION

Small temporal RNAs (stRNAs), also known as microRNAs (miRNAs), such as lin-4 and let-7 in *Caenorhabditis elegans* and let-7 in *Drosophila melanogaster* and humans encode no protein, but instead appear to block the productive translation of mRNA by binding sequences in the 3' untranslated region (3' UTR) of their target mRNAs. As described in Hutvágner et al., Science, 293:834 (Jul. 12, 2001), let-7 RNA in *Drosophila* has been shown to be cleaved from a larger precursor transcript, which is similar to the generation of small RNAs from a longer, structured precursor double-stranded RNA in the RNA interference (RNAi) pathway.

Figure 1:
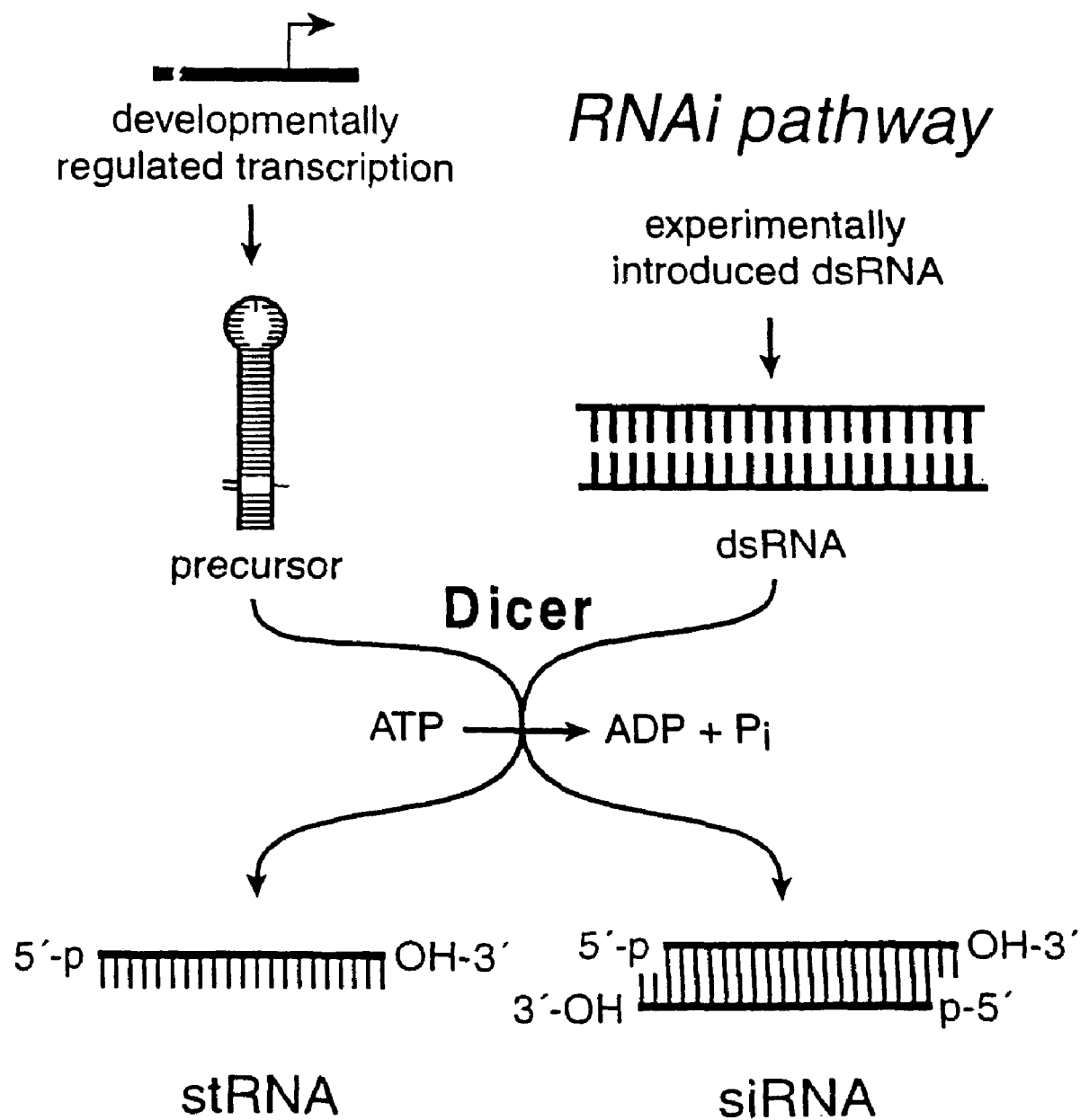
FIG. 1 is a schematic diagram of the dual nature of the stRNA and siRNA pathways.

Like siRNAs, stRNAs are also 21-25 nucleotides long, but unlike siRNAs, are single-stranded and do not mediate gene silencing via target mRNA cleavage. As shown in FIG. 1, the RNAi and stRNA pathways intersect; both require the RNA processing enzyme Dicer to produce the active small RNA components that repress gene expression. Dicer and perhaps other proteins act on pre-stRNAs to yield mature, single-stranded stRNAs that repress mRNA translation. In RNAi, Dicer cleaves long, double-stranded RNA to yield siRNA duplexes that mediate targeted mRNA destruction.

Whereas long, double-stranded RNAs are cleaved symmetrically by Dicer to generate duplex siRNAs, current evidence suggests that stRNAs are cleaved asymmetrically to generate only a single-stranded stRNA. stRNA precursors are stem-loop RNAs that do not mediate target cleavage or provoke the sequence non-specific responses induced by long, double-stranded RNA. On the other hand, the invention provides new, engineered RNA precursors that when processed within a cell generate siRNAs that mediated target cleavage. These siRNAs can be double- or single-stranded, as long as they mediate cleavage of the target mRNA. Such engineered RNA precursors can be expressed in transgenic mammals in a cell-type-specific or developmental-stage-specific manner to induce RNAi in a specific cell or cells at a defined time.

A *Drosophila* embryo lysate that mediates RNAi in vitro (Tuschl et al., (1999) cited supra), which process double-stranded RNA into siRNA (Zamore et al., (2000) cited supra), and pre-let-7-stRNA into mature let-7 stRNA (Hutvágner et al., (2001, cited supra), can be used to assay the ability of an engineered RNA precursor to mediate RNAi in vitro. This assay allows testing of the new engineered RNA precursors. The new engineered precursors differ from naturally occurring, wild-type stRNA precursors by various modifications and by the fact that one portion of their duplex stem comprises a nucleic acid sequence that is complementary, preferably fully complementary, to a portion of the mRNA of a target gene.

Engineered RNA Precursors that Generate siRNAs

Figure 2A:
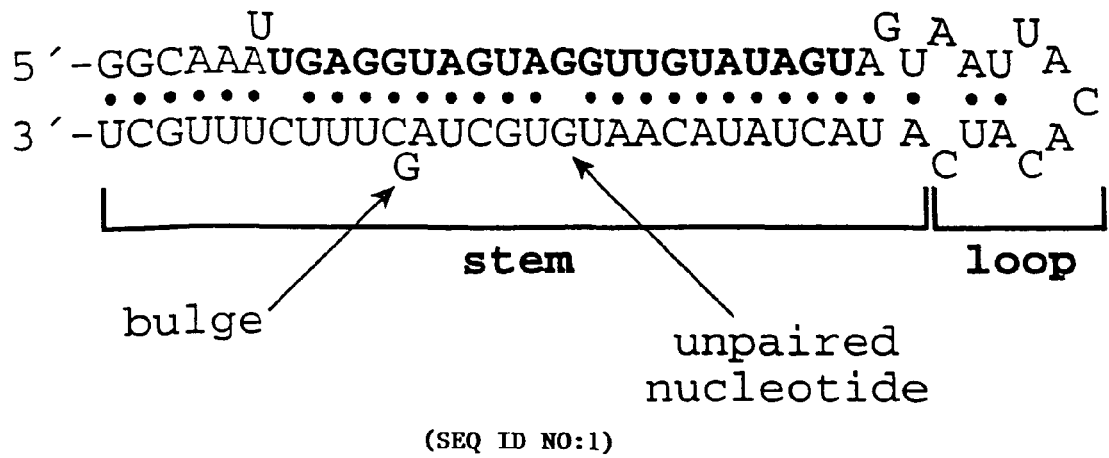
FIG. 2A is a schematic representation of a wild-type, stRNA precursor (SEQ ID NO:1).

Naturally-occurring stRNA precursors (pre-stRNA) have certain elements or components that are illustrated in FIG. 2A, which shows an stRNA precursor for let-7 (pre-let-7). Each precursor is a single strand that forms a duplex stem including two portions that are generally complementary, and a loop, that connects the two portions of the stem. In typical pre-stRNAs, the stem includes one or more bulges, e.g., extra nucleotides that create a single nucleotide "loop" in one portion of the stem, and/or one or more unpaired nucleotides that create a gap in the hybridization of the two portions of the stem to each other.

Engineered RNA precursors of the invention are artificial constructs that are similar to naturally occurring pre-stRNAs, but differ from the wild-type precursor sequences in a number of ways. The key difference is that one portion of the duplex stem is a nucleic acid sequence that is complementary (or anti-sense) to the target mRNA. Thus, engineered RNA precursors include a duplex stem with two portions and a loop connecting the two stem portions. The two stem portions are about 18 or 19 to about 25, 30, 35, 37, 38, 39, or 40 or more nucleotides in length. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us.

Other differences from natural pre-stRNA sequences include, but are not limited to, deleting unpaired or bulged nucleotides, introducing additional base-paired nucleotides to one or both of the stem portions, modifying the loop sequence to increase or decrease the number of paired nucleotides, or replacing all or part of the loop sequence with a tetraloop or other loop sequences. Thus, the loop in the engineered RNA precursors can be 2, 3, 4, 5, 6, 7, 8, 9, or more, e.g., 15 or 20, or more nucleotides in length. Tetraloop sequences can include, but are not limited to, the sequences GNRA (SEQ ID NO: 13), where N is any nucleotide and R is a purine nucleotide, GGGG (SEQ ID NO:14), and UUUU (SEQ ID NO:15).

Figure 2B:
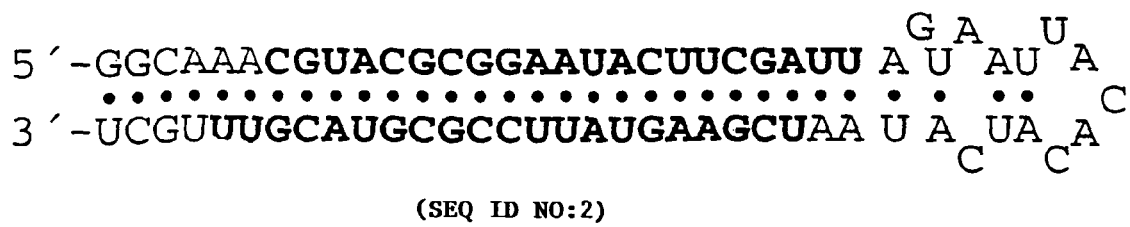
Figure 2C:
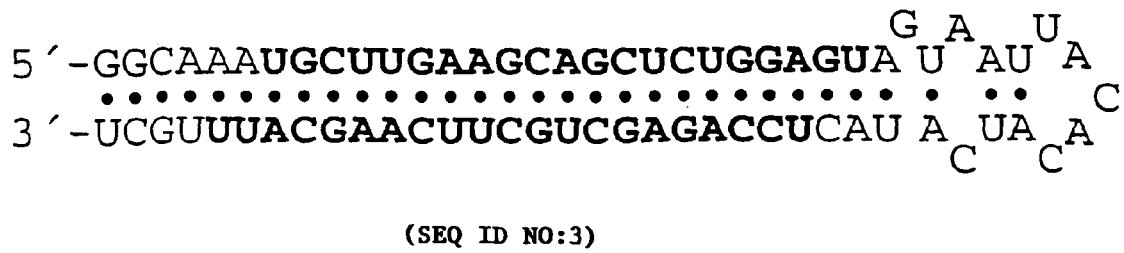

Four examples of such engineered RNA precursors are illustrated in FIGS. 2B to 2E. FIGS. 2B and 2C illustrate engineered precursors in which the stem portions have had all unpaired and bulging nucleotides removed or paired, but the loop is the same as the wild-type loop in the pre-stRNA. FIGS. 2D and 2E illustrate two engineered RNA precursors with a tetraloop. In FIG. 2D, the tetraloop UUUU (SEQ ID NO:15) replaces a portion of the wild-type loop in FIG. 2A. In FIG. 2E, the tetraloop GGGG (SEQ ID NO:14) replaces the entire wild-type loop sequence.

Figure 4D:
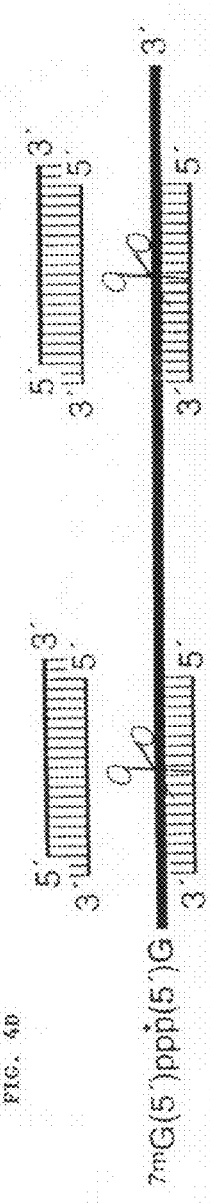
FIG. 4D is a schematic representation of a chimeric target mRNA for an in vitro luciferase/let-7 RNAi reaction. The sites of siRNA-directed target cleavage are indicated by "scissors."
Figure 4A:
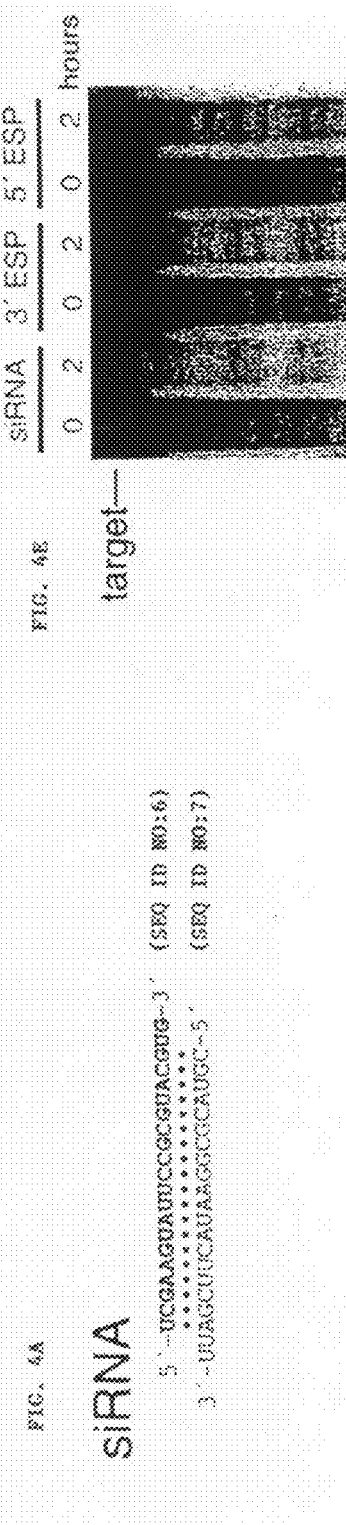
Figure 4B:
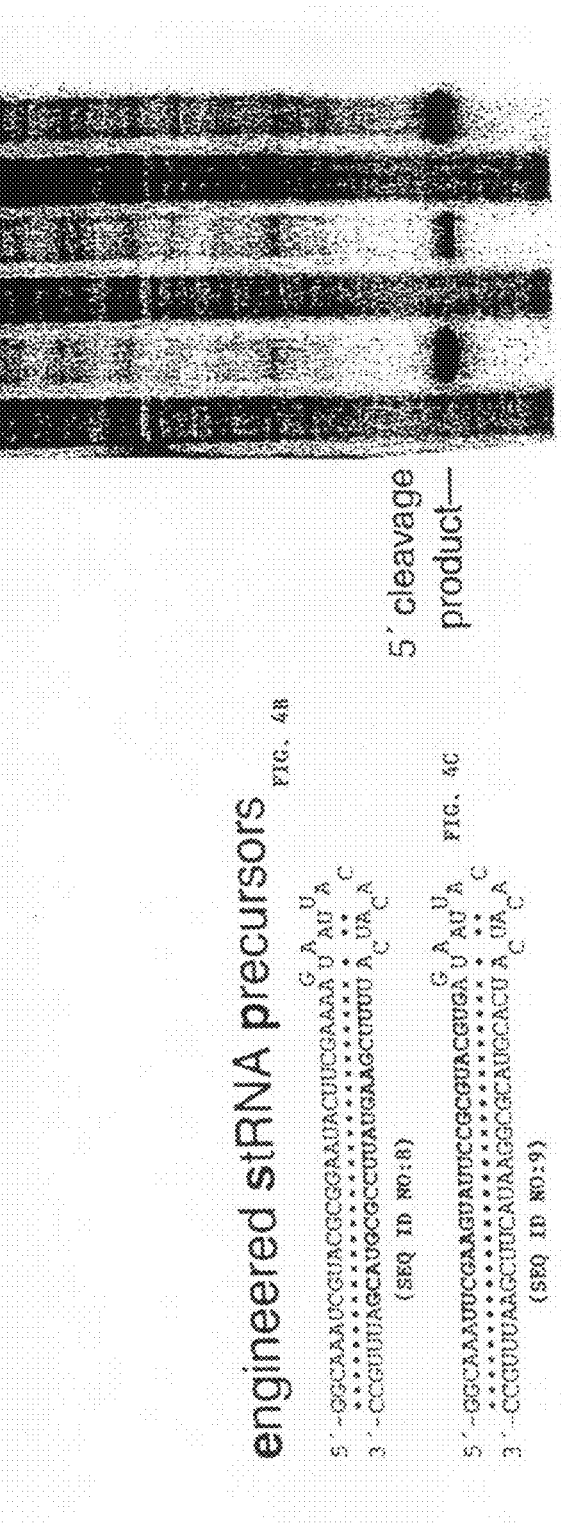

FIGS. 4B and 4C illustrate additional engineered RNA precursors. Each engineered RNA precursor includes in its stem a sequence that is perfectly complementary to a portion of the sequence of the firefly luciferase mRNA. In FIG. 4B (SEQ ID NO:8), this region is shown in bold type, and is located on the 3' side of the stem. In FIG. 4C (SEQ ID NO:9), this complementary sequence is on the 5' side of the stem. Unlike the naturally-occurring pre-let-7 RNA, these engineered RNA precursors have fully complementary stems, and direct RNAi against the luciferse mRNA.

In addition, modification of the naturally occurring stRNA precursor to generate an engineered RNA precursor (pre-siRNA) includes altering the sequence of the RNA to include the sequences of the desired siRNA duplex. The desired siRNA duplex, and thus both of the two stem portions in the engineered RNA precursor, are selected by methods known in the art. These include, but are not limited to, selecting an 18, 19, 20, 21 nucleotide, or longer, sequence from the target gene mRNA sequence from a region 100 to 200 or 300 nucleotides on the 3' side of the start of translation. In general, the sequence can be selected from any portion of the mRNA from the target gene, such as the 5' UTR (untranslated region), coding sequence, or 3' UTR. This sequence can optionally follow immediately after a region of the target gene containing two adjacent AA nucleotides. The last two nucleotides of the 21 or so nucleotide sequence can be selected to be UU (so that the anti-sense strand of the siRNA begins with UU). This 21 or so nucleotide sequence is used to create one portion of a duplex stem in the engineered RNA precursor. This sequence can replace a stem portion of a wild-type pre-stRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-stRNA.

Engineered RNA precursors include in the duplex stem the 21-22 or so nucleotide sequences of the siRNA desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor, and to maximize the efficacy of the resulting siRNA in targeting the corresponding mRNA for destruction by RNAi in vivo and in vitro.

Another defining feature of these engineered RNA precursors is that as a consequence of their length, sequence, and/or structure, they do not induce sequence non-specific responses, such as induction of the interferon response or apoptosis, or that they induce a lower level of such sequence non-specific responses than long, double-stranded RNA (>150 bp) currently used to induce RNAi. For example, the interferon response is triggered by dsRNA longer than 30 base pairs.

Transgenes Encoding Engineered RNA Precursors

The new engineered RNA precursors can be synthesized by standard methods known in the art, e.g., by use of an automated DNA synthesizer (such as are commercially available from Biosearch, Applied Biosystems, etc.). These synthetic, engineered RNA precursors can be used directly as described below or cloned into expression vectors by methods known in the field.

The engineered RNA precursors should be delivered to cells in vitro or in vivo in which it is desired to target a specific mRNA for destruction. A number of methods have been developed for delivering DNA or RNA to cells. For example, for in vivo delivery, molecules can be injected directly into a tissue site or administered systemically. In vitro delivery includes methods known in the art such as electroporation and lipofection.

To achieve intracellular concentrations of the nucleic acid molecule sufficient to suppress expression of endogenous mRNAs, one can use, for example, a recombinant DNA construct in which the oligonucleotide is placed under the control of a strong Pol III (e.g., U6 or PolIII H1-RNA promoter) or Pol II promoter. The use of such a construct to transfect target cells in vitro or in vivo will result in the transcription of sufficient amounts of the engineered RNA precursor to lead to the production of an siRNA that can target a corresponding mRNA sequence for cleavage by RNAi to decrease the expression of the gene encoding that mRNA. For example, a vector can be introduced in vivo such that it is taken up by a cell and directs the transcription of an engineered RNA precursor. Such a vector can remain episomal or become chromosomally integrated, as long as it can be transcribed to produce the desired stRNA precursor.

Such vectors can be constructed by recombinant DNA technology methods known in the art. Vectors can be plasmid, viral, or other vectors known in the art such as those described herein, used for replication and expression in mammalian cells or other targeted cell types. The nucleic acid sequences encoding the engineered RNA precursors can be prepared using known techniques. For example, two synthetic DNA oligonucleotides can be synthesized to create a novel gene encoding the entire engineered RNA precursor. The DNA oligonucleotides, which will pair, leaving appropriate 'sticky ends' for cloning, can be inserted into a restriction site in a plasmid that contains a promoter sequence (e.g., a Pol II or a Pol III promoter) and appropriate terminator sequences 3' to the engineered RNA precursor sequences (e.g., a cleavage and polyadenylation signal sequence from SV40 or a Pol III terminator sequence).

The invention also encompasses genetically engineered host cells that contain any of the foregoing expression vectors and thereby express the nucleic acid molecules of the invention in the host cell. The host cells can be cultured using known techniques and methods (see, e.g., Culture of Animal Cells (R. I. Freshney, Alan R. Liss, Inc. 1987); Molecular Cloning, Sambrook et al. (Cold Spring Harbor Laboratory Press, 1989)).

Successful introduction of the vectors of the invention into host cells can be monitored using various known methods. For example, transient transfection can be signaled with a reporter, such as a fluorescent marker, such as Green Fluorescent Protein (GFP). Stable transfection can be indicated using markers that provider the transfected cell with resistance to specific environmental factors (e.g., antibiotics and drugs), such as hygromycin B resistance, e.g., in insect cells and in mammalian cells.

Regulatory Sequences

The expression of the engineered RNA precursors is driven by regulatory sequences, and the vectors of the invention can include any regulatory sequences known in the art to act in mammalian cells, e.g., murine cells; in insect cells; in plant cells; or other cells. The term regulatory sequence includes promoters, enhancers, and other expression control elements. It will be appreciated that the appropriate regulatory sequence depends on such factors as the future use of the cell or transgenic animal into which a sequence encoding an engineered RNA precursor is being introduced, and the level of expression of the desired RNA precursor. A person skilled in the art would be able to choose the appropriate regulatory sequence. For example, the transgenic animals described herein can be used to determine the role of a test polypeptide or the engineered RNA precursors in a particular cell type, e.g., a hematopoietic cell. In this case, a regulatory sequence that drives expression of the transgene ubiquitously, or a hematopoietic-specific regulatory sequence that expresses the transgene only in hematopoietic cells, can be used. Expression of the engineered RNA precursors in a hematopoietic cell means that the cell is now susceptible to specific, targeted RNAi of a particular gene. Examples of various regulatory sequences are described below.

The regulatory sequences can be inducible or constitutive. Suitable constitutive regulatory sequences include the regulatory sequence of a housekeeping gene such as the α-actin regulatory sequence, or may be of viral origin such as regulatory sequences derived from mouse mammary tumor virus (MMTV) or cytomegalovirus (CMV).

Alternatively, the regulatory sequence can direct transgene expression in specific organs or cell types (see, e.g., Lasko et al., 1992, Proc. Natl. Acad. Sci. USA 89:6232). Several tissue-specific regulatory sequences are known in the art including the albumin regulatory sequence for liver (Pinkert et al., 1987, Genes Dev. 1:268-276); the endothelin regulatory sequence for endothelial cells (Lee, 1990, J. Biol. Chem. 265:10446-50); the keratin regulatory sequence for epidermis; the myosin light chain-2 regulatory sequence for heart (Lee et al., 1992, J. Biol. Chem. 267:15875-85), and the insulin regulatory sequence for pancreas (Bucchini et al., 1986, Proc. Natl. Acad. Sci. USA 83:2511-2515), or the vav regulatory sequence for hematopoietic cells (Oligvy et al., 1999, Proc. Natl. Acad. Sci. USA 96:14943-14948). Another suitable regulatory sequence, which directs constitutive expression of transgenes in cells of hematopoietic origin, is the murine MHC class I regulatory sequence (Morello et al., 1986, EMBO J. 5:1877-1882). Since MHC expression is induced by cytokines, expression of a test gene operably linked to this regulatory sequence can be upregulated in the presence of cytokines.

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals such as mice, include regulation by ecdysone, by estrogen, progesterone, tetracycline, chemical inducers of dimerization, and isopropyl-beta-D-1-thiogalactopyranoside (IPTG) (collectively referred to as "the regulatory molecule"). Each of these expression systems is well described in the literature and permits expression of the transgene throughout the animal in a manner controlled by the presence or absence of the regulatory molecule. For a review of inducible expression systems, see, e.g., Mills, 2001, Genes Devel. 15:1461-1467, and references cited therein.

The regulatory elements referred to above include, but are not limited to, the cytomegalovirus hCMV immediate early gene, the early or late promoters of SV40 adenovirus (Bernoist et al., *Nature*, 290:304, 1981), the tet system, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors. Additional promoters include the promoter contained in the 3' long terminal repeat of Rous sarcoma virus (Yamamoto et al., *Cell* 22:787-797, 1988); the herpes thymidine kinase promoter (Wagner et al., *Proc. Natl. Acad. Sci. USA* 78:1441, 1981); or the regulatory sequences of the metallothionein gene (Brinster et al., *Nature* 296:39, 1988).

Assay for Testing Engineered RNA Precursors

*Drosophila* embryo lysates can be used to determine if an engineered RNA precursor was, in fact, the direct precursor of a mature stRNA or siRNA. This lysate assay is described in Tuschl et al., 1999, supra, Zamore et al., 2000, supra, and Hutvágner et al. 2001, supra. These lysates recapitulate RNAi in vitro, thus permitting investigation into whether the proposed precursor RNA was cleaved into a mature stRNA or siRNA by an RNAi-like mechanism. Briefly, the precursor RNA is incubated with *Drosophila* embryo lysate for various times, then assayed for the production of the mature siRNA or stRNA by primer extension or Northern hybridization. As in the in vivo setting, mature RNA accumulates in the cell-free reaction. Thus, an RNA corresponding to the proposed precursor can be shown to be converted into a mature stRNA or siRNA duplex in the *Drosophila* embryo lysate.

Furthermore, an engineered RNA precursor can be functionally tested in the *Drosophila* embryo lysates. In this case, the engineered RNA precursor is incubated in the lysate in the presence of a 5' radiolabeled target mRNA in a standard in vitro RNAi reaction for various lengths of time. The target mRNA can be 5' radiolabeled using guanylyl transferase (as described in Tuschl et al., 1999, supra and references therein) or other suitable methods. The products of the in vitro reaction are then isolated and analyzed on a denaturing acrylamide or agarose gel to determine if the target mRNA has been cleaved in response to the presence of the engineered RNA precursor in the reaction. The extent and position of such cleavage of the mRNA target will indicate if the engineering of the precursor created a pre-siRNA capable of mediating sequence-specific RNAi.

Transgenic Animals

Engineered RNA precursors of the invention can be expressed in transgenic animals. These animals represent a model system for the study of disorders that are caused by, or exacerbated by, overexpression or underexpression (as compared to wild-type or normal) of nucleic acids (and their encoded polypeptides) targeted for destruction by the engineered RNA precursor products (siRNAs), and for the development of therapeutic agents that modulate the expression or activity of nucleic acids or polypeptides targeted for destruction.

Transgenic animals can be farm animals (pigs, goats, sheep, cows, horses, rabbits, and the like), rodents (such as rats, guinea pigs, and mice), non-human primates (for example, baboons, monkeys, and chimpanzees), and domestic animals (for example, dogs and cats). Invertebrates such as *Caenorhabditis elegans* or *Drosophila* can be used as well as non-mammalian vertebrates such as fish (e.g., zebrafish) or birds (e.g., chickens). Engineered RNA precursors with stems of 18 to 30 nucleotides in length are preferred for use in mammals, such as mice.

A transgenic founder animal can be identified based upon the presence of a transgene that encodes the new RNA precursors in its genome, and/or expression of the transgene in tissues or cells of the animals, for example, using PCR or Northern analysis. Expression is confirmed by a decrease in the expression (RNA or protein) of the target sequence.

A transgenic founder animal can be used to breed additional animals carrying the transgene. Moreover, transgenic animals carrying a transgene encoding the RNA precursors can further be bred to other transgenic animals carrying other transgenes. In addition, cells obtained from the transgenic founder animal or its offspring can be cultured to establish primary, secondary, or immortal cell lines containing the transgene.

Procedures for Making Transgenic Non-Human Animals

A number of methods have been used to obtain transgenic, non-human animals, which are animals that have gained an additional gene by the introduction of a transgene into their cells (e.g., both the somatic and germ cells), or into an ancestor's germ line. In some cases, transgenic animals can be generated by commercial facilities (e.g., The Transgenic *Drosophila* Facility at Michigan State University, The Transgenic Zebrafish Core Facility at the Medical College of Georgia (Augusta, Ga.), and Xenogen Biosciences (St. Louis, Mo.). In general, the construct containing the transgene is supplied to the facility for generating a transgenic animal.

Methods for generating transgenic animals include introducing the transgene into the germ line of the animal. One method is by microinjection of a gene construct into the pronucleus of an early stage embryo (e.g., before the four-cell stage; Wagner et al., 1981, Proc. Natl. Acad. Sci. USA 78:5016; Brinster et al., 1985, Proc. Natl. Acad. Sci. USA 82:4438). Alternatively, the transgene can be introduced into the pronucleus by retroviral infection. A detailed procedure for producing such transgenic mice has been described (see e.g., Hogan et al., *Manipulating the Mouse Embryo*, Cold Spring Harbour Laboratory, Cold Spring Harbour, N.Y. (1986); U.S. Pat. No. 5,175,383 (1992)). This procedure has also been adapted for other animal species (e.g., Hammer et al., 1985, Nature 315:680; Murray et al., 1989, Reprod. Fert. Devl. 1:147; Pursel et al., 1987, Vet. Immunol. Histopath. 17:303; Rexroad et al., 1990, J. Reprod. Fert. 41 (suppl):119; Rexroad et al., 1989, Molec. Reprod. Devl. 1:164; Simons et al., 1988, BioTechnology 6:179; Vize et al., 1988, J. Cell. Sci. 90:295; and Wagner, 1989, J. Cell. Biochem. 13B (suppl): 164).

In brief, the procedure involves introducing the transgene into an animal by microinjecting the construct into the pronuclei of the fertilized mammalian egg(s) to cause one or more copies of the transgene to be retained in the cells of the developing mammal(s). Following introduction of the transgene construct into the fertilized egg, the egg may be incubated in vitro for varying amounts of time, or reimplanted a in surrogate host, or both. One common method is to incubate the embryos in vitro for about 1-7 days, depending on the species, and then reimplant them into the surrogate host. The presence of the transgene in the progeny of the transgenically manipulated embryos can be tested by Southern blot analysis of a segment of tissue.

Another method for producing germ-line transgenic animals is through the use of embryonic stem (ES) cells. The gene construct can be introduced into embryonic stem cells by homologous recombination (Thomas et al., 1987, Cell 51:503; Capecchi, Science 1989, 244:1288; Joyner et al., 1989, Nature 338:153) in a transcriptionally active region of the genome. A suitable construct can also be introduced into embryonic stem cells by DNA-mediated transfection, such as by electroporation (Ausubel et al., *Current Protocols in Molecular Biology*, John Wiley & Sons, 1987). Detailed procedures for culturing embryonic stem cells (e.g., ES-D3, ATCC# CCL-1934, ES-E14TG2a, ATCC# CCL-1821, American Type Culture Collection, Rockville, Md.) and methods of making transgenic animals from embryonic stem cells can be found in *Teratocarcinomas and Embryonic Stem Cells, A Practical Approach*, ed. E. J. Robertson (IRL Press, 1987). In brief, the ES cells are obtained from pre-implantation embryos cultured in vitro (Evans et al., 1981, Nature 292:154-156). Transgenes can be efficiently introduced into ES cells by DNA transfection or by retrovirus-mediated transduction. The resulting transformed ES cells can thereafter be combined with blastocysts from a non-human animal. The ES cells colonize the embryo and contribute to the germ line of the resulting chimeric animal.

In the above methods, the transgene can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann et al., 1995, Proc. Natl. Acad. Sci. USA 92:1292). A plasmid is a DNA molecule that can replicate autonomously in a host.

The transgenic, non-human animals can also be obtained by infecting or transfecting cells either in vivo (e.g., direct injection), ex vivo (e.g., infecting the cells outside the host and later reimplanting), or in vitro (e.g., infecting the cells outside host), for example, with a recombinant viral vector carrying a gene encoding the engineered RNA precursors. Examples of suitable viral vectors include recombinant retroviral vectors (Valerio et al., 1989, Gene 84:419; Scharfman et al., 1991, Proc. Natl. Acad. Sci. USA 88:462; Miller and Buttimore, 1986, Mol. Cell. Biol. 6:2895), recombinant adenoviral vectors (Freidman et al., 1986, Mol. Cell. Biol. 6:3791; Levrero et al., 1991, Gene 101:195), and recombinant Herpes simplex viral vectors (Fink et al., 1992, Human Gene Therapy 3:11). Such methods are also useful for introducing constructs into cells for uses other than generation of transgenic animals.

Other approaches include insertion of transgenes encoding the new engineered RNA precursors into viral vectors including recombinant adenovirus, adeno-associated virus, and herpes simplex virus-1, or recombinant bacterial or eukaryotic plasmids. Viral vectors transfect cells directly. Other approaches include delivering the transgenes, in the form of plasmid DNA, with the help of, for example, cationic liposomes (lipofectin) or derivatized (e.g. antibody conjugated) polylysine conjugates, gramacidin S, artificial viral envelopes, or other such intracellular carriers, as well as direct injection of the transgene construct or $CaPO_4$ precipitation carried out in vivo. Such methods can also be used in vitro to introduce constructs into cells for uses other than generation of transgenic animals.

Retrovirus vectors and adeno-associated virus vectors can be used as a recombinant gene delivery system for the transfer of exogenous genes in vivo or in vitro. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, 1990, Blood 76:271). A replication-defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals.

Examples of suitable retroviruses include pLJ, pZIP, pWE and pEM which are known to those skilled in the art. Examples of suitable packaging virus lines for preparing both ecotropic and amphotropic retroviral systems include Psi-Crip, Psi-Cre, Psi-2 and Psi-Am. Retroviruses have been used to introduce a variety of genes into many different cell types, including epithelial cells, in vitro and/or in vivo (see for example Eglitis, et al., 1985, Science 230:1395-1398; Danos and Mulligan, 1988, Proc. Natl. Acad. Sci. USA 85:6460-6464; Wilson et al., 1988, Proc. Natl. Acad. Sci. USA 85:3014-3018; Armentano et al., 1990, Proc. Natl. Acad. Sci. USA 87:6141-6145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem et al., 1992, Proc. Natl. Acad. Sci. USA 89:7640-7644; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In another example, recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

Another viral gene delivery system useful in the present invention also utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988, BioTechniques 6:616), Rosenfeld et al. (1991, Science 252:431-434), and Rosenfeld et al. (1992, Cell 68:143-155). Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al., 1992, cited supra). Furthermore, the virus particle is relatively stable and amenable to purification and concentration, and as above, can be modified to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham, 1986, J. Virol. 57:267).

Yet another viral vector system useful for delivery of the subject transgenes is the adeno-associated virus (AAV). Adeno-associated virus is a naturally occurring defective virus that requires another virus, such as an adenovirus or a herpes virus, as a helper virus for efficient replication and a productive life cycle. For a review, see Muzyczka et al. (1992, Curr. Topics in Micro. and Immunol. 158:97-129). It is also one of the few viruses that may integrate its DNA into non-dividing cells, and exhibits a high frequency of stable integration (see for example Flotte et al. (1992, Am. J. Respir. Cell. Mol. Biol. 7:349-356; Samulski et al., 1989, J. Virol. 63:3822-3828; and McLaughlin et al. (1989, J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

In addition to viral transfer methods, such as those illustrated above, non-viral methods can also be employed to cause expression of an engineered RNA precursor of the invention in the tissue of an animal. Most non-viral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject gene of the invention by the targeted cell. Exemplary gene delivery systems of this type include liposomal derived systems, poly-lysine conjugates, and artificial viral envelopes. Other embodiments include plasmid injection systems such as are described in Meuli et al., (2001) *J. Invest. Dermatol.*, 116(1):131-135; Cohen et al., (2000) *Gene Ther.*, 7(22):1896-905; and Tam et al., (2000) *Gene Ther.*, 7(21):1867-74.

In a representative embodiment, a gene encoding an engineered RNA precursor of the invention can be entrapped in liposomes bearing positive charges on their surface (e.g., lipofectins) and (optionally) which are tagged with antibodies against cell surface antigens of the target tissue (Mizuno et al., (1992) *No Shinkei Geka*, 20:547-551; PCT publication WO91/06309; Japanese patent application 1047381; and European patent publication EP-A-43075).

Animals harboring the transgene can be identified by detecting the presence of the transgene in genomic DNA (e.g., using Southern analysis). In addition, expression of the engineered RNA precursor can be detected directly (e.g., by Northern analysis). Expression of the transgene can also be confirmed by detecting a decrease in the amount of protein corresponding to the targeted sequence. When the transgene is under the control of an inducible or developmentally regulated promoter, expression of the target protein is decreased when the transgene is induced or at the developmental stage when the transgene is expressed, respectively.

Clones of Transgenic Animals

Clones of the non-human transgenic animals described herein can be produced according to the methods described in Wilmut et al. ((1997) Nature, 385:810-813) and PCT publication Nos. WO 97/07668 and WO 97/07669. In brief, a cell, e.g., a somatic cell from the transgenic animal, can be isolated and induced to exit the growth cycle and enter the $G_o$ phase to become quiescent. The quiescent cell can then be fused, e.g., through the use of electrical pulses, to an enucleated oocyte from an animal of the same species from which the quiescent cell is isolated. The reconstructed oocyte is then cultured such that it develops into a morula or blastocyte and is then transferred to a pseudopregnant female foster animal. Offspring borne of this female foster animal will be clones of the animal from which the cell, e.g., the somatic cell, was isolated.

Once the transgenic animal is produced, cells of the transgenic animal and cells from a control animal are screened to determine the presence of an RNA precursor nucleic acid sequence, e.g., using polymerase chain reaction (PCR). Alternatively, the cells can be screened to determine if the RNA precursor is expressed (e.g., by standard procedures such as Northern blot analysis or reverse transcriptase-polymerase chain reaction (RT-PCR); Sambrook et al., Molecular Cloning—A Laboratory Manual, (Cold Spring Harbor Laboratory, 1989)).

The transgenic animals of the present invention can be homozygous or heterozygous, and one of the benefits of the invention is that the target mRNA is effectively degraded even in heterozygotes. The present invention provides for transgenic animals that carry a transgene of the invention in all their cells, as well as animals that carry a transgene in some, but not all of their cells. That is, the invention provides for mosaic animals. The transgene can be integrated as a single transgene or in concatamers, e.g., head-to-head tandems or head-to-tail tandems.

For a review of techniques that can be used to generate and assess transgenic animals, skilled artisans can consult Gordon (*Intl. Rev. Cytol.* 115:171-229, 1989), and may obtain additional guidance from, for example: Hogan et al. "Manipulating the Mouse Embryo" (Cold Spring Harbor Press, Cold Spring Harbor, N.Y., 1986; Krimpenfort et al., *Bio/Technology* 9:86, 1991; Palmiter et al., *Cell* 41:343, 1985; Kraemer et al., "Genetic Manipulation of the Early Mammalian Embryo," Cold Spring Harbor Press, Cold Spring Harbor, N.Y., 1985; Hammer et al., *Nature* 315:680, 1985; Purcel et al., *Science,* 244:1281, 1986; Wagner et al., U.S. Pat. No. 5,175,385; and Krimpenfort et al., U.S. Pat. No. 5,175,384.

Transgenic Plants

Among the eukaryotic organisms featured in the invention are plants containing an exogenous nucleic acid that encodes an engineered RNA precursor of the invention.

Accordingly, a method according to the invention comprises making a plant having a nucleic acid molecule or construct, e.g., a transgene, described herein. Techniques for introducing exogenous nucleic acids into monocotyledonous and dicotyledonous plants are known in the art, and include, without limitation, *Agrobacterium*-mediated transformation, viral vector-mediated transformation, electroporation and particle gun transformation, see, e.g., U.S. Pat. Nos. 5,204,253 and 6,013,863. If a cell or tissue culture is used as the recipient tissue for transformation, plants can be regenerated from transformed cultures by techniques known to those skilled in the art. Transgenic plants can be entered into a breeding program, e.g., to introduce a nucleic acid encoding a polypeptide into other lines, to transfer the nucleic acid to other species or for further selection of other desirable traits. Alternatively, transgenic plants can be propagated vegetatively for those species amenable to such techniques. Progeny includes descendants of a particular plant or plant line. Progeny of a plant include seeds formed on $F_1$, $F_2$, $F_3$, and subsequent generation plants, or seeds formed on $BC_1$, $BC_2$, $BC_3$, and subsequent generation plants. Seeds produced by a transgenic plant can be grown and then selfed (or outcrossed and selfed) to obtain seeds homozygous for the nucleic acid encoding a novel polypeptide.

A suitable group of plants with which to practice the invention include dicots, such as safflower, alfalfa, soybean, rapeseed (high erucic acid and canola), or sunflower. Also suitable are monocots such as corn, wheat, rye, barley, oat, rice, millet, amaranth or sorghum. Also suitable are vegetable crops or root crops such as potato, broccoli, peas, sweet corn, popcorn, tomato, beans (including kidney beans, lima beans, dry beans, green beans) and the like. Also suitable are fruit crops such as peach, pear, apple, cherry, orange, lemon, grapefruit, plum, mango and palm. Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panicum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* and *Zea.*

The nucleic acid molecules of the invention can be expressed in plants in a cell- or tissue-specific manner according to the regulatory elements chosen to include in a particular nucleic acid construct present in the plant. Suitable cells, tissues, and organs in which to express a chimeric polypeptide of the invention include, without limitation, egg cell, central cell, synergid cell, zygote, ovule primordia, nucellus, integuments, endothelium, female gametophyte cells, embryo, axis, cotyledons, suspensor, endosperm, seed coat, ground meristem, vascular bundle, cambium, phloem, cortex, shoot or root apical meristems, lateral shoot or root meristems, floral meristem, leaf primordia, leaf mesophyll cells, and leaf epidermal cells, e.g., epidermal cells involved in forming the cuticular layer. Also suitable are cells and tissues grown in liquid media or on semi-solid media.

Transgenic Fungi

Other eukaryotic organisms featured in the invention are fungi containing an exogenous nucleic acid molecule that encodes an engineered RNA precursor of the invention.

Accordingly, a method according to the invention comprises introducing a nucleic acid molecule or construct as described herein into a fungus. Techniques for introducing exogenous nucleic acids into many fungi are known in the art, see, e.g., U.S. Pat. Nos. 5,252,726 and 5,070,020. Transformed fungi can be cultured by techniques known to those skilled in the art. Such fungi can be used to introduce a nucleic acid encoding a polypeptide into other fungal strains, to transfer the nucleic acid to other species or for further selection of other desirable traits.

A suitable group of fungi with which to practice the invention include fission yeast and budding yeast, such as *Saccharomyces cereviseae*, *S. pombe*, *S. carlsbergeris* and *Candida albicans*. Filamentous fungi such as *Aspergillus* spp. and *Penicillium* spp. are also useful.

Pharmaceutical Compositions

The molecules of the invention can be incorporated into pharmaceutical compositions. Such compositions typically include a nucleic acid molecule, e.g., a nucleic acid molecule (e.g., a transgene) that encodes an engineered RNA precursor, or the precursor RNA itself, and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, inhalation, transdermal (topical), transmucosal, and rectal administration. Administration can also be oral. Solutions or suspensions used for parenteral administration such as intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel3, or corn starch; a lubricant such as magnesium stearate or Sterotes3; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of compositions of the invention lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of a composition containing a sequence that encodes an engineered RNA precursor, or the precursor itself (i.e., an effective dosage), is an amount that inhibits expression of the polypeptide encoded by the target gene by at least 30 percent. Higher percentages of inhibition, e.g., 45, 50, 75, 85, 90 percent or higher may be preferred in certain embodiments. Exemplary doses include milligram or microgram amounts of the molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. The compositions can be administered one time per week for between about 1 to 10 weeks, e.g., between 2 to 8 weeks, or between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. In some cases transient expression of the engineered RNA precursor may be desired. When an inducible promoter is included in the construct encoding an engineered RNA precursor, expression is assayed upon delivery to the subject of an appropriate dose of the substance used to induce expression.

It is furthermore understood that appropriate doses of a composition depend upon the potency of the molecule (the sequence encoding the engineered precursor) with respect to the expression or activity to be modulated. When one or more of these molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be generally inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted expression or activity of any gene that is transcribed. As used herein, the term "treatment" is defined as the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. A therapeutic agent is an engineered RNA precursor of the invention, or a nucleic acid molecule (DNA) that encodes the precursor.

With regards to both prophylactic and therapeutic methods of treatment, such treatments may be specifically tailored or modified, based on knowledge obtained about a subject's genome, specifically knowledge about a gene sequence (i.e., mutated gene) whose expression is associated with disease. Thus, a molecule of the invention can be engineered, based on knowledge of the gene whose expression is targeted, to inhibit expression of that gene as described herein.

Thus, in one aspect, the invention provides a method for treating in a subject, a disorder, e.g., a disease or condition, associated with an aberrant or unwanted gene expression or activity, by administering to the subject an engineered nucleic acid sequence that encodes an engineered precursor RNA.

Subjects at risk for a disorder which is caused or contributed to by aberrant or unwanted expression or activity of a gene can be identified by, for example, any or a combination of diagnostic or prognostic assays that are known in the art. Administration of a prophylactic agent can occur prior to the manifestation of symptoms characteristic of the aberrance, such that a disease or disorder is prevented or, alternatively, delayed in its progression.

The molecules of the invention can act as novel therapeutic agents for controlling one or more of cellular proliferative and/or differentiative disorders, disorders associated with bone metabolism, immune disorders, hematopoietic disorders, cardiovascular disorders, liver disorders, viral diseases, pain or metabolic disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer," "hyperproliferative," and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

In general, the engineered RNA precursors of the invention are designed to target genes associated with particular disorders. Examples of such genes associated with proliferative disorders that can be targeted include activated ras, p53, BRCA-1, and BRCA-2. Other specific genes that can be targeted are those associated with amyotrophic lateral sclerosis (ALS; e.g., superoxide dismutase-1 (SOD1)); Huntington's disease (e.g., huntingtin), Parkinson's disease (parkin), and genes associated with autosomal dominant disorders.

The engineered RNAs of the invention can be used to treat a variety of immune disorders, in particular those associated with overexpression of a gene or expression of a mutant gene. Examples of hematopoieitic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure. coronary artery disease, valvular disease, arrhythmias, and cardiomyopathies.

Disorders which may be treated by methods described herein include, but are not limited to, disorders associated with an accumulation in the liver of fibrous tissue, such as that resulting from an imbalance between production and degradation of the extracellular matrix accompanied by the collapse and condensation of preexisting fibers.

Additionally, molecules of the invention can be used to treat viral diseases, including but not limited to hepatitis B, hepatitis C, herpes simplex virus (HSV), HIV-AIDS, poliovirus, and smallpox virus. Molecules of the invention are engineered as described herein to target expressed sequences of a virus, thus ameliorating viral activity and replication. The molecules can be used in the treatment and/or diagnosis of viral infected tissue. Also, such molecules can be used in the treatment of virus-associated carcinoma, such as hepatocellular cancer.

Uses of Engineered RNA Precursors to Induce RNAi

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism.

For example, one may be seeking to discover a small molecule that reduces the activity of a kinase whose overexpression leads to unrestrained cell proliferation. This kinase is overexpressed in a variety of cancer cells. A key question to be determined is whether or not decreasing the activity of this kinase in adult mammals would have unexpected deleterious effects. By expressing an engineered RNA precursor that targets for destruction by the RNAi pathway the mRNA encoding the kinase throughout the tissues of an adult mouse, the deleterious effects of such a potential drug can be determined. That is, the method described here will allow rapid assessment of the suitability of the kinase as a drug target.

The new nucleic acid molecules that encode the engineered RNA precursors can also be used to create large numbers of cells or vectors in microarrays in which each cell or vector in the array includes nucleic acid molecules that encode an engineered RNA precursor that is specific for a different target gene. See, e.g., Ziauddin et al., Nature, 411:107-110 (2001).

EXAMPLES

The invention is further described in the following examples, which do not limit the scope of the invention described in the claims.

Example 1

Producing an Engineered RNA Precursor

To produce an engineered RNA precursor that will target a gene for firefly luciferase for cleavage, the sequence of the coding portion of the mRNA from firefly luciferase was examined to select a suitable sequence. At a position more than 100 nucleotides, but less than 300 nucleotides, 3' to the start of translation, the sequence CGUACGCGGAAUACU-UCGAUU (SEQ ID NO:16) was found immediately after the sequence AA. Since this sequence meets the criteria for selection of an siRNA, it was chosen. An engineered precursor RNA was then designed that includes this sequence (underlined) as represented below (and shown in FIG. 2B):

(SEQ ID NO: 2)
5'-GGCAAACGUACGCGGAAUACUUCGAUUAGUAAUUACACAUCAUAAU

CGAAGUAUUCCGCGUACGUUUGCU-3'

Synthetic deoxyoligonucleotide sequences were prepared that serve as an in vitro transcription template for preparing this engineered RNA precursor using the enzyme T7 RNA Polymerase according to published protocols. Below are shown the two deoxyoligonucleotides. The oligonucleotides contain the sequence of the T7 RNA Polymerase promoter (underlined in the top strand) to facilitate in vitro transcription into RNA.

Top oligo:
(SEQ ID NO: 17)
5'-GCGTAATACGACTCACTATAGGCAAACGTACGCGGAATAGTTCGATTA

GTAATTACACATCATAATCGAAGTATTCCGCGTACGTTTGCT-3'

Bottom oligo:
(SEQ ID NO: 18)
5'-TGTAGTCACGTACGCGGAATACTTCGAAGAAACGAGTAATTACTAAAT

CGAAGTATTCCGCGTACGTTTGCCTATAGTGAGTCGTATTACGC-3'

Next, the double-stranded DNA was formed by annealing the two deoxyoligonucleotides and was transcribed into RNA using T7 RNA Polymerase. The resulting engineered RNA precursor was purified by standard means, and then tested for its ability to promote cleavage of the target mRNA in vitro in a standard RNAi reaction.

Briefly, firefly luciferase mRNA was prepared by in vitro transcription and radiolabeled using $\alpha$-$^{32}$P-GTP and Guanylyl Transferase as described previously (Tuschl et al., (1999) cited supra) to generate a radioactive target mRNA. The radioactive target mRNA was incubated in a standard in vitro RNAi reaction with *Drosophila* embryo lysate and 50 nM engineered RNA precursor (ESP) for 0 and 3 hours as described previously (Tuschl et al., (1999) cited supra). The reaction products were isolated and analyzed by denaturing acrylamide gel electrophoresis as described previously (Zamore et al., (2000) cited supra). As shown in FIG. 3, the engineered RNA precursor induced sequence-specific cleavage of the radioactive target mRNA (5' cleavage product). Thus, the precursor was shown to mediate RNAi. FIG. 3 also shows the RNA cleavage product of a standard siRNA (also incubated for 0 and 3 hours), which produced the same sequence-specific 5' cleavage product as the ESP.

Example 2

Engineered let-7 Precursor RNAs Asymmetrically Trigger RNAi In Vitro

Two engineered let-7 RNA precursors (ESPs) were prepared in which the stem of pre-let-7 (FIGS. 4B and 4C) was altered to contain a sequence complementary to firefly luciferase. Because most stRNAs begin with uracil, the ESPs were designed so that the luciferase-complementary sequence (anti-sense luciferase) began with U. Since stRNAs can be encoded on either the 5' or the 3' side of the precursor hairpin (e.g., on either stem) the anti-sense luciferase sequence (in bold) was placed on the 3' side of the stem in one ESP (3' ESP) (FIG. 4B) and on the 5' side in the second stem (5' ESP) (FIG. 4C).

The ESP RNAs were prepared as generally described in Example 1 by using the following DNA oligonucleotide pairs to generate partially single-stranded T7 RNA Polymerase transcription templates:

(SEQ ID NO: 19)
5'-GTAATACGACTCACTATAG-3'

(SEQ ID NO: 20)
5'-GGCAAATTCGAAGTATTCCGCGTACGTGATGATGTGTAATTACTCAC

GTACGCGGAATACTTCGAATTTGCCTATAGTGAGTCGTATTAC-3'

(5' ESP)

(SEQ ID NO: 21)
5'-GGCAAATCGTACGCGGAATACTTCGAAAATGATGTGTAATTACTTT

TCGAAGTATTCCGCGTACGATTTGCCTATAGTGAGTCGTATTAC-3'

(3' ESP)

The anti-sense firefly luciferase target RNA has been described previously (A. Nykänen, B. Haley, P. D. Zamore, Cell 107, 309, 2001).

The ability of each ESP to direct luciferase-specific RNAi in an in vitro reaction was tested against a target mRNA (shown schematically in FIG. 4D) containing a portion of the firefly luciferase mRNA and a sequence fully complementary to let-7 (the target was constructed by standard techniques and synthesized using T7 RNA Polymerase). As a control, an siRNA duplex containing the anti-sense luciferase sequence was used (FIG. 4A).

FIG. 4E is an autoradiograph showing the results of an assay for determining whether the 5' and 3' ESPs can equally promote cleavage of the target RNA in vitro (the assay conditions are described in Example 1, except the ESPs and control were incubated for 0 and 2 hours). Both the 3' and the 5' ESPs directed cleavage of the target RNA within the luciferase sequences, the same site cleaved when the RNAi reaction was programmed with the control siRNA.

Example 3

Preparing a Transgene Encoding an Engineered RNA Precursor

To prepare a transgene encoding an engineered precursor to target destruction of the luciferase mRNA in a transgenic mouse that expresses firefly luciferase mRNA in all of its cells, the engineered RNA precursor sequence described in Example 1 is cloned by standard recombinant DNA methods into a nucleic acid molecule, e.g., a vector containing a constitutively expressed promoter sequence and the desired nucleic acid sequence (transgene) encoding the engineered RNA precursor as illustrated in FIG. 5. This vector will also contain sequences appropriate for its introduction into ES cells to produce transgenic mice by standard methods. The resulting transgene expresses the engineered RNA precursor in all cells of a transgenic mouse.

The engineered precursor RNA is then processed by Dicer and other components of the RNAi machinery to yield an siRNA directed against the firefly luciferase gene. This siRNA directs cleavage of the luciferase mRNA, resulting in a decrease in the expression of luciferase mRNA in the cells of the animal.

The same methods can be used to silence other target genes, either using constitutively expressed or inducible expression systems in a variety of transgenic animals.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of making an engineered ribonucleic acid (RNA) precursor comprising the steps of:
   (a) selecting a wild-type miRNA or stRNA precursor sequence; and
   (b) modifying the wild-type precursor sequence to produce an engineered RNA precursor comprising
      (i) a first stem portion comprising a sequence of about 18 to about 40 nucleotides that is substantially complementary to a sequence of a messenger RNA (mRNA) of a target gene of the mammalian cell;
      (ii) a second stem portion comprising a sequence of about 18 to about 40 nucleotides that is sufficiently complementary to the about 18 to about 40 nucleotide sequence of the first stem portion to hybridize with the first stem portion to form a duplex stem; and
      (iii) a loop portion that connects the two stem portions, such that the engineered RNA precursor, when expressed in a cell, is processed by the cell to produce a duplex siRNA that mediates RNA interference (RNAi) by selectively cleaving the mRNA,
   wherein the wild-type precursor sequence is modified by incorporating the sequence of the siRNA duplex.

2. The method of claim 1, wherein the wild-type precursor sequence is modified such that the sequence of about 18 to about 40 nucleotides of the first stem portion is fully complementary to the sequence of the mRNA.

3. The method of claim 1, wherein the wild-type precursor sequence is modified such that the second stem portion is substantially complementary to the about 18 to about 40 nucleotide sequence of the first stem portion.

4. The method of claim 1, wherein the second stem portion is fully complementary to the about 18 to about 40 nucleotide sequence of the first stem portion.

5. The method of claim 1, wherein the wild-type precursor sequence is modified by replacing all or part of the loop portion of the pre-stRNA sequence.

6. The method of claim 1, wherein the first stem portion is located at the 5' end of the engineered RNA precursor.

7. The method of claim 1, wherein the first stem portion is located at the 3' end of the engineered RNA precursor.

8. The method of claim 1, wherein the loop portion comprises at least 4 nucleotides.

9. The method of claim 1, wherein the loop portion comprises at least 7 nucleotides.

10. The method of claim 1, wherein the loop portion comprises 11 nucleotides.

11. The method of claim 1, wherein the sequence of the mRNA is located from 100 to 300 nucleotides 3' of the start of translation of the mRNA.

12. The method of claim 1, wherein the sequence of the mRNA is located in a 5' untranslated region (UTR) or a 3' UTR of the mRNA.

13. The method of claim 1, wherein the loop portion of the engineered RNA precursor is at least 4 nucleotides in length and comprises a sequence from a loop of the naturally-occurring stRNA or miRNA precursor.

14. The method of claim 1, wherein the number of nucleotides in the loop portion of the engineered RNA precursor differs from the number of nucleotides in the loop of the naturally-occurring stRNA or miRNA precursor.

15. The method of claim 1, wherein the sequence of the loop portion of the engineered RNA precursor is the same as the sequence from the loop of the naturally-occurring stRNA or miRNA precursor.

16. The method of claim 1, wherein the first stem portion is 18 to 40 nucleotides in length and the second stem portion is 18 to 40 nucleotides in length.

17. The method of claim 1, wherein the first stem portion is 18 to 30 nucleotides in length; and the sequence of the second stem portion is 18 to 30 nucleotides in length.

18. The method of claim 1, wherein the first stem portion is 22 to 28 nucleotides in length and the second stem portion is 22 to 28 nucleotides in length.

19. The method of claim 1, wherein the first and second stem portions each comprise the same number of nucleotides.

20. The method of claim 1, wherein one of the first and second stem portions comprises 1 to 4 more nucleotides than the other stem portion.

21. The method of claim 1, wherein said first stem portion or said second stem portion further comprises an overhang of 1, 2, 3, or 4 nucleotides.

22. The method of claim 21, wherein said overhang comprises two uracils.

23. The method of claim 1, wherein the target gene is a human gene.

24. The method of claim 1, wherein the target gene is a mutant human gene.

25. The method of claim 1, wherein the target gene is a viral gene.

26. The method of claim 1, wherein the precursor is processed by Dicer.

27. A method of inducing RNAi of a target gene in a mammalian cell in vivo, the method comprising
   (i) contacting the cell with an isolated nucleic acid molecule comprising a regulatory sequence operably linked to a nucleic acid sequence that encodes an engineered RNA precursor comprising
      (I) a first stem portion comprising a sequence of about 18 to about 40 nucleotides that is substantially complementary to a sequence of a messenger RNA (mRNA) of a target gene of the mammalian cell;

(II) a second stem portion comprising a sequence of about 18 to about 40 nucleotides that is sufficiently complementary to the about 18 to about 40 nucleotide sequence of the first stem portion to hybridize with the first stem portion to form a duplex stem; and (III) a loop portion that connects the two stem portions, wherein the engineered precursor is made according to the method of claim 1; and (ii) inducing the cell to express the engineered RNA precursor, wherein the precursor is processed by the cell to produce the duplex siRNA that mediates RNAi by selectively cleaving the mRNA, thereby inducing RNAi of the target gene in the cell.

28. The method of claim 27, wherein the sequence of about 18 to about 40 nucleotides of the first stem portion is fully complementary to the sequence of the mRNA.

29. The method of claim 27, wherein the second stem portion is substantially complementary to the about 18 to about 40 nucleotide sequence of the first stem portion.

30. The method of claim 27, wherein the second stem portion is fully complementary to the about 18 to about 40 nucleotide sequence of the first stem portion.

31. The method of claim 27, wherein the first stem portion is located at the 5' end of the engineered RNA precursor.

32. The method of claim 27, wherein the first stem portion is located at the 3' end of the engineered RNA precursor.

33. The method of claim 27, wherein the loop portion comprises at least 4 nucleotides.

34. The method of claim 27, wherein the loop portion comprises at least 7 nucleotides.

35. The method of claim 27, wherein the loop portion comprises 11 nucleotides.

36. The method of claim 27, wherein the sequence of the mRNA is located from 100 to 300 nucleotides 3' of the start of translation of the mRNA.

37. The method of claim 27, wherein the sequence of the mRNA is located in a 5' untranslated region (UTR) or a 3' UTR of the mRNA.

38. The method of claim 27, wherein the loop portion of the engineered RNA precursor is at least 4 nucleotides in length and comprises a sequence from a loop of a naturally-occurring stRNA or miRNA precursor.

39. The method of claim 38, wherein the number of nucleotides in the loop portion of the engineered RNA precursor differs from the number of nucleotides in the loop of the naturally-occurring stRNA or miRNA precursor.

40. The method of claim 38, wherein the sequence of the loop portion of the engineered RNA precursor is the same as the sequence from the loop of the naturally-occurring stRNA or miRNA precursor.

41. The method of claim 27, wherein the first stem portion is 18 to 40 nucleotides in length and the second stem portion is 18 to 40 nucleotides in length.

42. The method of claim 27, wherein the first stem portion is 18 to 30 nucleotides in length; and the sequence of the second stem portion is 18 to 30 nucleotides in length.

43. The method of claim 27, wherein the first stem portion is 22 to 28 nucleotides in length and the second stem portion is 22 to 28 nucleotides in length.

44. The method of claim 27, wherein the first and second stem portions each comprise the same number of nucleotides.

45. The method of claim 27, wherein one of the first and second stem portions comprises 1 to 4 more nucleotides than the other stem portion.

46. The method of claim 27, wherein said first stem portion or said second stem portion further comprises an overhang of 1, 2, 3, or 4 nucleotides.

47. The method of claim 46, wherein said overhang comprises two uracils.

48. The method of claim 27, wherein the target gene is a human gene.

49. The method of claim 27, wherein the target gene is a mutant human gene.

50. The method of claim 47, wherein the target gene is a viral gene.

51. The method of claim 47, wherein the precursor is processed by Dicer.

52. A method of making an engineered ribonucleic acid (RNA) precursor comprising the steps of:

(a) selecting a wild-type miRNA or stRNA precursor sequence; and (b) modifying the wild-type precursor sequence to produce an engineered RNA precursor comprising (i) a first stem portion comprising a sequence of about 18 to about 40 nucleotides that is substantially complementary to a sequence of a messenger RNA (mRNA) of a target gene of the mammalian cell;

(ii) a second stem portion comprising a sequence of about 18 to about 40 nucleotides that is sufficiently complementary to the about 18 to about 40 nucleotide sequence of the first stem portion to hybridize with the first stem portion to form a duplex stem; and (iii) a loop portion that connects the two stem portions, such that the engineered RNA precursor, when expressed in a cell, is processed by the cell to produce a duplex siRNA that mediates RNA interference (RNAi) by selectively cleaving the, wherein the wild-type precursor sequence is modified by deleting or pairing unpaired or bulged nucleotides in one or both of the stem portions of the pre-stRNA sequence.

53. The method of claim 52, wherein the wild-type precursor sequence is modified such that the sequence of about 18 to about 40 nucleotides of the first stem portion is fully complementary to the sequence of the mRNA.

54. The method of claim 52, wherein the wild-type precursor sequence is modified such that the second stem portion is substantially complementary to the about 18 to about 40 nucleotide sequence of the first stem portion.

55. The method of claim 52, wherein the second stem portion is fully complementary to the about 18 to about 40 nucleotide sequence of the first stem portion.

56. The method of claim 52, wherein the wild-type precursor sequence is modified by replacing all or part of the loop portion of the pre-stRNA sequence.

57. The method of claim 52, wherein the first stem portion is located at the 5' end of the engineered RNA precursor.

58. The method of claim 52, wherein the first stem portion is located at the 3' end of the engineered RNA precursor.

59. The method of claim 52, wherein the loop portion comprises at least 4 nucleotides.

60. The method of claim 52, wherein the loop portion comprises at least 7 nucleotides.

61. The method of claim 52, wherein the loop portion comprises 11 nucleotides.

62. The method of claim 52, wherein the sequence of the mRNA is located from 100 to 300 nucleotides 3' of the start of translation of the mRNA.

63. The method of claim 52, wherein the sequence of the mRNA is located in a 5' untranslated region (UTR) or a 3' UTR of the mRNA.

64. The method of claim 52, wherein the loop portion of the engineered RNA precursor is at least 4 nucleotides in length and comprises a sequence from a loop of the naturally-occurring stRNA or miRNA precursor.

65. The method of claim 52, wherein the number of nucleotides in the loop portion of the engineered RNA precursor differs from the number of nucleotides in the loop of the naturally-occurring stRNA or miRNA precursor.

66. The method of claim 52, wherein the sequence of the loop portion of the engineered RNA precursor is the same as the sequence from the loop of the naturally-occurring stRNA or miRNA precursor.

67. The method of claim 52, wherein the first stem portion is 18 to 40 nucleotides in length and the second stem portion is 18 to 40 nucleotides in length.

68. The method of claim 52, wherein the first stem portion is 18 to 30 nucleotides in length; and the sequence of the second stem portion is 18 to 30 nucleotides in length.

69. The method of claim 52, wherein the first stem portion is 22 to 28 nucleotides in length and the second stem portion is 22 to 28 nucleotides in length.

70. The method of claim 52, wherein the first and second stem portions each comprise the same number of nucleotides.

71. The method of claim 52, wherein one of the first and second stem portions comprises 1 to 4 more nucleotides than the other stem portion.

72. The method of claim 52, wherein said first stem portion or said second stem portion further comprises an overhang of 1, 2, 3, or 4 nucleotides.

73. The method of claim 72, wherein said overhang comprises two uracils.

74. The method of claim 52, wherein the target gene is a human gene.

75. The method of claim 52, wherein the target gene is a mutant human gene.

76. The method of claim 52, wherein the target gene is a viral gene.

77. The method of claim 52, wherein the precursor is processed by Dicer.

78. A method of inducing RNAi of a target gene in a mammalian cell in vivo, the method comprising contacting the cell with engineered RNA precursor comprising
(I) a first stem portion comprising a sequence of about 18 to about 40 nucleotides that is substantially complementary to a sequence of a messenger RNA (mRNA) of a target gene of the mammalian cell;
(II) a second stem portion comprising a sequence of about 18 to about 40 nucleotides that is sufficiently complementary to the about 18 to about 40 nucleotide sequence of the first stem portion to hybridize with the first stem portion to form a duplex stem; and
(III) a loop portion that connects the two stem portions, wherein the precursor is made according to the method of claim 52, and wherein the precursor is processed by the cell to produce the duplex siRNA that mediates RNAi by selectively cleaving the mRNA thereby inducing RNAi of the target gene in the cell.

79. The method of claim 78, wherein the sequence of about 18 to about 40 nucleotides of the first stem portion is fully complementary to the sequence of the mRNA.

80. The method of claim 78, wherein the second stem portion is substantially complementary to the about 18 to about 40 nucleotide sequence of the first stem portion.

81. The method of claim 78, wherein the second stem portion is fully complementary to the about 18 to about 40 nucleotide sequence of the first stem portion.

82. The method of claim 78, wherein the first stem portion is located at the 5' end of the engineered RNA precursor.

83. The method of claim 78, wherein the first stem portion is located at the 3' end of the engineered RNA precursor.

84. The method of claim 78, wherein the loop portion comprises at least 4 nucleotides.

85. The method of claim 78, wherein the loop portion comprises at least 7 nucleotides.

86. The method of claim 78, wherein the loop portion comprises 11 nucleotides.

87. The method of claim 78, wherein the sequence of the mRNA is located from 100 to 300 nucleotides 3' of the start of translation of the mRNA.

88. The method of claim 78, wherein the sequence of the mRNA is located in a 5' untranslated region (UTR) or a 3' UTR of the mRNA.

89. The method of claim 78, wherein the loop portion of the engineered RNA precursor is at least 4 nucleotides in length and comprises a sequence from a loop of a naturally-occurring stRNA or miRNA precursor.

90. The method of claim 89, wherein the number of nucleotides in the loop portion of the engineered RNA precursor differs from the number of nucleotides in the loop of the naturally-occurring stRNA or miRNA precursor.

91. The method of claim 89, wherein the sequence of the loop portion of the engineered RNA precursor is the same as the sequence from the loop of the naturally-occurring stRNA or miRNA precursor.

92. The method of claim 78, wherein the first stem portion is 18 to 40 nucleotides in length and the second stem portion is 18 to 40 nucleotides in length.

93. The method of claim 78, wherein the first stem portion is 18 to 30 nucleotides in length; and the sequence of the second stem portion is 18 to 30 nucleotides in length.

94. The method of claim 78, wherein the first stem portion is 22 to 28 nucleotides in length and the second stem portion is 22 to 28 nucleotides in length.

95. The method of claim 78, wherein the first and second stem portions each comprise the same number of nucleotides.

96. The method of claim 78, wherein one of the first and second stem portions comprises 1 to 4 more nucleotides than the other stem portion.

97. The method of claim 78, wherein said first stem portion or said second stem portion further comprises an overhang of 1, 2, 3, or 4 nucleotides.

98. The method of claim 78, wherein said overhang comprises two uracils.

99. The method of claim 78, wherein the target gene is a human gene.

100. The method of claim 78, wherein the target gene is a mutant human gene.

101. The method of claim 78, wherein the target gene is a viral gene.

102. The method of claim 78, wherein the precursor is processed by Dicer.

103. A method of inducing RNAi of a target gene in a mammalian cell in vivo, the method comprising:
(i) contacting the cell with an isolated nucleic acid molecule comprising a regulatory sequence operably linked to a nucleic acid sequence that encodes an engineered ribonucleic acid (RNA) precursor, wherein the precursor comprises a stem from naturally-occurring stRNA or miRNA precursor, the stem comprising a first stem portion of about 18 to about 40 nucleotides and a second stem portion of about 18 to about 40 nucleotides, wherein the first stem portion comprises an stRNA or miRNA sequence within additional stem sequences of the first stem portion, and wherein the second stem portion comprises a sequence complementary to the stRNA or miRNA sequence within additional stem sequences of the second stem portion, wherein:
  (a) the stRNA or miRNA sequence within the first stem portion and the sequence within the second stem portion that is complementary to the stRNA or miRNA sequence are replaced with a siRNA antisense strand sequence that is complementary to a sequence of a messenger RNA (mRNA) of the target gene in the mammalian cell and a siRNA sense strand sequence that is complementary to the siRNA antisense strand sequence;
  (b) the second stem portion is sufficiently complementary to the first stem portion to hybridize with the first stem portion to form a duplex stem;
  (c) a loop portion connects the two stem portions, and
  (d) the engineered RNA precursor is processed by the cell to generate an siRNA that mediates cleavage of the mRNA; and
  (ii) inducing the cell to express the engineered RNA precursor encoded by the isolated nucleic acid to form the siRNA within the cell, thereby inducing RNAi of the target gene in the cell.

104. The method of claim 103, wherein the siRNA antisense strand sequence is fully complementary to the sequence of the mRNA.

105. The method of claim 103, wherein the siRNA sense strand sequence is fully complementary to the siRNA antisense strand sequence.

106. The method of claim 103, wherein the first stem portion is located at the 5' end of the engineered RNA precursor.

107. The method of claim 103, wherein the first stem portion is located at the 3' end of the engineered RNA precursor.

108. The method of claim 103, wherein the loop portion comprises at least 4 nucleotides.

109. The method of claim 103, wherein the loop portion comprises at least 7 nucleotides.

110. The method of claim 103, wherein the loop portion comprises 11 nucleotides.

111. The method of claim 103, wherein the sequence of the mRNA is located from 100 to 300 nucleotides 3' of the start of translation of the mRNA of the target gene.

112. The method of claim 103, wherein the sequence of the mRNA is located in a 5' untranslated region (UTR) or a 3' UTR of the mRNA of the target gene.

113. The method of claim 103, wherein the loop portion of the engineered RNA precursor is at least 4 nucleotides in length and comprises a sequence from a loop of the naturally-occurring stRNA or miRNA precursor.

114. The method of claim 113, wherein the number of nucleotides in the loop portion of the engineered RNA precursor differs from the number of nucleotides in the loop of the naturally-occurring stRNA or miRNA precursor.

115. The method of claim 113, wherein the sequence of the loop portion of the engineered RNA precursor is the same as the sequence from the loop of the naturally-occurring stRNA or miRNA precursor.

116. The method of claim 103, wherein first stem portion is 18 to 40 nucleotides in length and the second stem portion is 18 to 40 nucleotides in length.

117. The method of claim 103, wherein the first stem portion is 18 to 30 nucleotides in length and the second stem portion is 18 to 30 nucleotides in length.

118. The method of claim 103, wherein the first stem portion is 22 to 28 nucleotides in length and the second stem portion is 22 to 28 nucleotides in length.

119. The method of claim 103, wherein the first and second stem portions each comprise the same number of nucleotides.

120. The method of claim 103, wherein one of the first and second stem portions comprises 1 to 4 more nucleotides than the other stem portion.

121. The method of claim 103, wherein the first stem portion or the second stem portion further comprises an overhang of 1, 2, 3, or 4 nucleotides.

122. The method of claim 121, wherein the overhang comprises two uracils.

123. The method of claim 103, wherein the regulatory sequence comprises a Pol III or Pol II promoter.

124. The method of claim 123, wherein the Pol III promoter is a U6 or H1-RNA promoter.

125. The method of claim 123, wherein the regulatory sequence is constitutive or inducible.

126. The method of claim 123, wherein the regulatory sequence is a mammalian regulatory sequence.

127. The method of claim 126, wherein the mammalian regulatory sequence is tissue-specific regulatory sequence.

128. The method of claim 103, wherein the sequence of the engineered RNA precursor comprises a sequence selected from the group consisting of the sequence set forth in SEQ ID NO: 2, 3, 4, 5, 8 and 9.

129. The method of claim 103, wherein the sequence of the nucleic acid molecule comprises a sequence selected from the group consisting of SEQ ID NO: 10, 11, 17, 18, 20, 21 or a complement thereof.

130. The method of claim 103, wherein the target gene is a human gene.

131. The method of claim 103, wherein the target gene is a mutant human gene.

132. The method of claim 103, wherein the target gene is a viral gene.

133. The method of claim 103, wherein the precursor is processed by Dicer.

134. The method of claim 103, wherein the siRNA sequences are about 21 to about 25 nucleotides in length.

135. The method of claim 103, wherein the siRNA sequences are 21 or 22 nucleotides in length.

136. The method of claim 103, wherein the cell is a human cell.

137. A method of inducing ribonucleic acid interference (RNAi) of a target gene in a mammalian cell in vivo, the method comprising:
  contacting the cell with an engineered RNA precursor comprising a stem from a naturally-occurring stRNA or miRNA precursor, the stem comprising a first stem portion of about 18 to about 40 nucleotides and a second stem portion of about 18 to about 40 nucleotides, wherein the first stem portion comprises an stRNA or miRNA sequence within additional stem sequences of the first stem portion, and wherein the second stem portion comprises a sequence complementary to the stRNA or miRNA sequence within additional stem sequences of the second stem portion, wherein:
    (a) the stRNA or miRNA sequence within the first stem portion and the sequence within the second stem portion that is complementary to the stRNA or miRNA sequence are replaced with a siRNA antisense strand sequence that is complementary to a portion of a messenger RNA (mRNA) of the target gene in the mammalian cell and a siRNA sense strand sequence that is complementary to the siRNA antisense strand sequence;

(b) the second stem portion is sufficiently complementary to the first stem portion to hybridize with the first stem portion to form a duplex stem;

(c) a loop portion connects the two stem portions, and (d) the engineered RNA precursor is processed by the cell to generate an siRNA that mediates cleavage of the mRNA, thereby inducing RNAi of the target gene in the cell.

138. The method of claim 137, wherein the siRNA antisense strand sequence is fully complementary to the sequence of the mRNA.

139. The method of claim 137, wherein the siRNA sense strand sequence is fully complementary to the siRNA antisense strand sequence.

140. The method of claim 137, wherein the first stem portion is located at the 5' end of the engineered RNA precursor.

141. The method of claim 137, wherein the first stem portion is located at the 3' end of the engineered RNA precursor.

142. The method of claim 137, wherein the loop portion comprises at least 4 nucleotides.

143. The method of claim 137, wherein the loop portion comprises at least 7 nucleotides.

144. The method of claim 137, wherein the loop portion comprises 11 nucleotides.

145. The method of claim 137, wherein the sequence of the mRNA is located from 100 to 300 nucleotides 3' of the start of translation of the mRNA of the target gene.

146. The method of claim 137, wherein the sequence of the mRNA is located in a 5' untranslated region (UTR) or a 3' UTR of the mRNA of the target gene.

147. The method of claim 137, wherein the loop portion of the engineered RNA precursor is at least 4 nucleotides in length and comprises a sequence from a loop of the naturally-occurring stRNA or miRNA precursor.

148. The method of claim 147, wherein the number of nucleotides in the loop portion of the engineered RNA precursor differs from the number of nucleotides in the loop of the naturally-occurring stRNA or miRNA precursor.

149. The method of claim 147, wherein the sequence of the loop portion of the engineered RNA precursor is the same as the sequence from the loop of the naturally-occurring stRNA or miRNA precursor.

150. The method of claim 137, wherein first stem portion is 18 to 40 nucleotides in length and the second stem portion is 18 to 40 nucleotides in length.

151. The method of claim 137, wherein the first stem portion is 18 to 30 nucleotides in length and the second stem portion is 18 to 30 nucleotides in length.

152. The method of claim 137, wherein the first stem portion is 22 to 28 nucleotides in length and the second stem portion is 22 to 28 nucleotides in length.

153. The method of claim 137, wherein the first and second stem portions each comprise the same number of nucleotides.

154. The method of claim 137, wherein one of the first and second stem portions comprises 1 to 4 more nucleotides than the other stem portion.

155. The method of claim 137, wherein the first stem portion or the second stem portion further comprises an overhang of 1, 2, 3, or 4 nucleotides.

156. The method of claim 155, wherein the overhang comprises two uracils.

157. The method of claim 137, wherein the sequence of the engineered RNA precursor comprises a sequence selected from the group consisting of the sequence set forth in SEQ ID NO: 2, 3, 4, 5, 8 and 9.

158. The method of claim 137, wherein the target gene is a human gene.

159. The method of claim 137, wherein the target gene is a mutant human gene.

160. The method of claim 137, wherein the target gene is a viral gene.

161. The method of claim 137, wherein the precursor is processed by Dicer.

162. The method of claim 137, wherein the siRNA sequences are about 21 to about 25 nucleotides in length.

163. The method of claim 137, wherein the siRNA sequences are 21 or 22 nucleotides in length.

164. The method of claim 137, wherein the cell is a human cell.

* * * * *

UNITED STATES PATENT AND TRADEMARK OFFICE
CERTIFICATE OF CORRECTION

| | |
|---|---|
| PATENT NO. | : 7,893,036 B2 |
| APPLICATION NO. | : 12/079531 |
| DATED | : February 22, 2011 |
| INVENTOR(S) | : Phillip D. Zamore et al. |

It is certified that error appears in the above-identified patent and that said Letters Patent is hereby corrected as shown below:

In the Claims:

Claim 52, column 36, line 33 of the printed patent,

Please delete "(RNAi) by selectively cleaving the," and add "(RNAi) by selectively cleaving the mRNA,".

Signed and Sealed this
Tenth Day of May, 2011

David J. Kappos
*Director of the United States Patent and Trademark Office*